United States Patent [19]

Yanaihara et al.

[11] Patent Number: 4,855,406

[45] Date of Patent: Aug. 8, 1989

[54] ONCOGENE-RELATED PEPTIDES

[75] Inventors: Noboru Yanaihara, Shizuoka; Kaoru Abe, Yokosuka, both of Japan

[73] Assignee: Noboru Yanaihara et al., Shizuoka, Japan

[21] Appl. No.: 72,191

[22] Filed: Jul. 10, 1987

Related U.S. Application Data

[63] Continuation-in-part of Ser. No. 927,614, Nov. 6, 1986.

[30] Foreign Application Priority Data

Jul. 11, 1986 [JP]  Japan ................... 61-164331

[51] Int. Cl.$^4$ ..................... C07K 7/06; C07K 7/08; C07K 7/10
[52] U.S. Cl. ................................ 530/324; 530/325; 530/326; 530/327; 530/328
[58] Field of Search ............... 530/324, 325, 326, 327, 530/328

[56] References Cited

FOREIGN PATENT DOCUMENTS

| | | |
|---|---|---|
| 0190033 | 8/1986 | European Pat. Off. . |
| 0203587 | 12/1986 | European Pat. Off. . |
| 254530 | 11/1986 | Japan . |
| 108157 | 5/1987 | Japan . |

OTHER PUBLICATIONS

Chem. Abstr., vol. 98 (1983), 84318.
Chem. Abstr., vol. 103 (1985), 117327.
Chem. Abstr., vol. 104 (1986), 46533.
Chem. Abstr., vol. 104 (1986), 32530.
Report on Research for Comprehensive 10-year Strategy of Cancer Control by the Ministry of Health and Welfare in Fiscal 1984, pp. 103–107, issued Mar. 31, 1985, in Japan, by Abe et al.
Proceedings of the 44th Annual Melting of the Japanese Cancer Association, published on Sep. 28, 1985, in Japan, p. 433, item 1605, by Yamaguchi et al.
Proceedings of the 44th Annual Melting of the Japanese Cancer Association published on Sep. 28, 1985, in Japan, p. 433, item 1607, by Noguchi et al.
Derwent publication of EP-107053-A, published on May 2, 1984.
Derwent published of JA 60-028993, published on Feb. 14, 1985.
Derwent publication of JA 60-067432, published on Apr. 17, 1985.
Derwent Publication of JA 60-142925, published on Jul. 29, 1985.
Report on Research for Comprehensive 10-Year Strategy of Cancer Control by the Ministry of Health and Welfare in Fiscal 1985, pp. 95–100, issued 3/31/86 in Japan, by Abe et al.
Proceedings of the 106th Annual Congress of the Japan Pharmaceutical Society Held on Apr. 2nd to 4th, 1986, p. 655, item 2M 10-4, published 3/10/86 in Japan, by Kazuaki Iguchi et al.
FEBS Letters, vol. 196, No. 2, Feb. 1986, pp. 301–304, by Atsumi Tsujimoto et al.
Program of the 24th Radioimmunoassay Research Society of Japan held on Nov. 30, 1985, in Tokyo, Japan, item 5, by Iguchi et al.
Derwent publication of JA 61-057598, published Mar. 24, 1986; Jpn. J. Cancer Res. (Gann), 77, 615–619, published on Jul. 31, 1986, in Japan by Yamaguchi et al.
Biomedical Research 7 (5) 365–367, 1986, by Suzuki et al; and Proceedings of the 45th Annual Melting of the Japanese Cancer Association, item 1930, published Sep. 30, 1986, by Dobashi et al.

*Primary Examiner*—Delbert R. Phillips
*Attorney, Agent, or Firm*—Armstrong, Nikaido, Marmelstein, Kubovcik & Murray

[57] ABSTRACT

Disclosed are an oncogene-related peptide characterized in that the peptide comprises a portion of the amino acid sequence of a gene product coded for by an oncogene, an antigen or immunogen formed from the oncogene-related peptide and a carrier, an antibody against such antigen or immunogen, and a method of determining a gene product coded for by an oncogene by an immunoreaction with use of such antibody.

15 Claims, 19 Drawing Sheets

Retention Time (min)

ONCOGENE-RELATED PEPTIDES

This application is a continuation-in-part of application Ser. No. 927,614 filed Nov. 6, 1986.

The present invention relates to novel peptides related to various oncogene products.

Recent gene technological studies have been made for structural elucidation of various oncogenes in human and animal tumor cells, and the total structure of cancer proteins which are oncogene products have been reported (HAMLYN P. et al., (1983), Oncogenes, Lancet, 11, 326–329, KRONTIRIS T. G. (1983), The Emerging Genetics of Human Cancer, New Engl J. Med., 309, 404–409, Report on Research for Comprehensive 10-Year Strategy of Cancer Control by the Ministry of Health and Welfare in Fiscal 1985, pp. 13–17, issued on Mar. 31, 1986, etc.).

To promote research on cancer proteins at molecular level in the present situation, it has been desired to provide means for determining (detecting) or purifying cancer proteins to eventually permit diagnosis of cancers.

An object of the present invention is to provde such means, and more particularly to provide an antibody having specific reactivity on the desired cancer protein.

Another object of the invention is to provide a specific peptide serviceable as a hapten for producing the antibody.

Another object of the invention is to provide a technique for determining the desired cancer protein or the antibody against the protein (antiserum found in cancer patient).

The present invention provides an oncogene-related peptide characterized in that the peptide comprises a portion of the amino acid sequence of a gene product coded for by an oncogene.

Stated more specifically, the present invention provides novel peptides (oncogene-related peptides) specified by the following amino acid sequences. The oncogene-related peptides of the present invention are hereinafter referred to by the following symbols.

<c-myc-related peptides>

H-Asn-Tyr-Asp-Leu-Asp-Tyr-Asp-Ser-Val-Gln-Pro-Tyr-Phe-Tyr-OH
(Symbol: "c-myc (11–24)")
H-Thr-Pro-Pro-Thr-Thr-Ser-Ser-Asp-Ser-Glu-Glu-Glu-Gln-Glu-Asp-Glu-Glu-Ile-Asp-Val-Val-Ser-Val-Glu-OH
(Symbol: "c-myc (244–268)")
R'-Arg-Arg-Glu-Gln-Leu-Lys-His-Lys-Leu-Glu-Gln-Leu-Arg-Asn-Ser-OH
(wherein R' is H, H-Leu-Arg-Lys- or H-Ala-Thr-Ala-Tyr-Ile-Leu-Ser-Val-Gln-Ala-Glu-Glu-Gln-Lys-Leu-Ile-Ser-Glu-Glu-Asp-Leu-Leu-Arg-Lys-)
(Symbol: "c-myc (423–437)" when R' is H, "c-myc (420–437)" when R' is H-Leu-Arg-Lys-, or "c-myc (399–437)" when R' is H-Ala-Thr-Ala-Tyr-Ile-Leu-Ser-Val-Gln-Ala-Glu-Glu-Gln-Lys-Leu-Ile-Ser-Glu-Glu-Asp-Leu-Leu-Arg-Lys-)

<HPV-related peptides>

H-Arg-Ser-Ser-Arg-Thr-Arg-Arg-Glu-Thr-Gln-Leu-OH
(Symbol: "HPV18 (E6) (148–158)")
H-Lys-Gln-Gln-Leu-Leu-Arg-Arg-Glu-Val-Tyr-Asp-Phe-Ala-Phe-Arg-Asp-Leu-OH
(Symbol: "HPV 18 (E6) (41–57)")

<hst-related peptides>

H-Tyr-Glu-Ser-Tyr-Lys-Tyr-Pro-Gly-Met-Phe-Ile-Ala-Leu-Ser-Lys-Asn-Gly-Lys-Thr-OH
(Symbol: "hst (169–187)")
H-His-Ala-Asp-Thr-Arg-Asp-Ser-Leu-Leu-Glu-Leu-Ser-Pro-Val-Glu-Arg-Gly-Val-Val-Ser-Ile-Phe-Gly-Val-Ala-Ser-OH
(Symbol: "hst (108–133)")

<Peptides related to ras gene product>

H-Tyr-Gly-Ala-Val-Gly-Val-Gly-Lys-Ser-OH
(Symbol: "ras-gene-product (10–18)")

<N-ras-related peptide>

H-Arg-Lys-Gln-Val-Val-Ile-Asp-Gly-Glu-Thr-OH
(Symbol: "N-ras (41–50)")

<B-lym-1-related peptide>

H-Leu-Ala-Ile-Asp-Ser-Leu-Tyr-Ser-Leu-Gln-Phe-Ala-Gly-Gly-Asn-OH
(Symbol: "B-lym-1 (44–58)")

<h-TGF-α-related peptide>

H-Val-Val-Ser-His-Phe-Asn-Asp-OH
(Symbol: "h-TGF-α(1–7)")

H—Val—Cys—His—Ser—Gly—Tyr—Val—Gly—Ala—
|
Arg—Cys—Glu—His—Ala—Asp—Leu—Leu—Ala—OH (Symbol: "h-TGF-α (33–50)")

<c-fos-related peptides>

H-Ser-Pro-Glu-Glu-Glu-Glu-Lys-Arg-Arg-Ile-Arg-Arg-Glu-Arg-Asn-Lys-Met-Ala-OH
(Symbol: "c-fos (133–150)")
H-Ala-Ala-Lys-Cys-Arg-Asn-Arg-Arg-Arg-Glu-Leu-Thr-Asp-OH
(Symbol: "c-fos (151–163)")
H-Thr-Asp-Gln-Leu-Glu-Asp-Glu-Lys-Ser-Ala-Leu-Gln-OH
(Symbol: "c-fos (169–180)")

<c-raf-1-related peptide>

H-Ser-Gln-His-Arg-Tyr-Ser-Thr-Pro-His-Ala-Phe-Thr-Phe-Asn-Thr-Ser-Ser-Pro-Ser-Ser-Glu-Gly-OH
(Symbol: "c-raf-1 (1–22)")
H-His-Gly-Asp-Val-Ala-Val-Lys-Ile-Leu-Lys-Val-Val-Asp-Pro-Thr-Pro-Glu-Gln-Phe-Gln-Ala-Phe-Arg-Asn-Glu-Val-Ala-Val-Leu-OH
(Symbol: "c-raf-1 (142–170)")
H-Leu-His-Arg-Ala-Ala-His-Thr-Glu-Asp-Ile-Asn-Ala-Cys-Thr-Leu-Thr-Thr-Ser-Pro-Arg-Leu-Pro-Val-Phe-OH
(Symbol: "c-raf-1 (398–421)")

<N-myc-related peptide>

H-Gly-Phe-Ala-Glu-His-Ser-Ser-Glu-Pro-Pro-Ser-Trp-Val-Thr-Glu-Met-Leu-Leu-Glu-Asn-Glu-Leu-OH
(Symbol: "N-myc (48–69)

<HTLV-PX-related peptides>

H-Pro-Glu-His-Gln-Ile-Thr-Trp-Asp-Pro-Ile-Asp-Gly-Arg-OH
(Symbol: "HTLV-PX-I")

H-Ile-Pro-Arg-Leu-Pro-Ser-Phe-Pro-Thr-Gln-Arg-Thr-Ser-Lys-Thr-Leu-Lys-OH
(Symbol: "HTLV-PX-II")

The symbols as used herein for amino acids, peptides, protective groups, active groups, etc. are those stipulated by IUPAC or those conventional in the art. Examples of such symbols are as follows. When optical isomers can be present for amino acids, etc., such isomers are herein given in L form unless otherwise specified.

Ala: alanine
Asp: aspartic acid
Asn: asparagine
Ile: isoleucine
Leu: leucine
Met: methionine
Pro: proline
Ser: serine
Glu: glutamic acid
Gln: glutamine
His: histidine
Arg: arginine
Phe: phenylalanine
Thr: threonine
Val: valine
Cys: cysteine
Tyr: tyrosine
Lys: lysine
Tos: p-toluenesulfonyl group
Boc: tert-butoxycarbonyl group
Bzl: benzyl group
MeBzl: p-methoxybenzyl group
OBzl: benzyloxy group
$Cl_2Bzl$: 2,6-dichlorobenzyl group
Cl-Z: 2-chlorobenzyloxycarbonyl group
Br-Z: 2-bromobenzyloxycarbonyl group
OcHex: cyclohexyloxy group Each of the above peptides provided by the present invention is thought to be an antigen recognition site specific to the corresponding oncogene product. Accordingly, the immunogen or antigen prepared with use of the present peptide as a hapten eadily and stably affords a large quantity of antibody which has specific reactivity on the oncogene product, i.e. cancer protein, corresponding to the hapten used.

The specific antibody thus obtained is usable, for example, for affinity chromatography when fixed as by being combined with a carrier therefor to use the antibody for purifying the corresponding cancer protein. The specific antibody is also usable for various immunoassays of the cancer protein. The peptide of the present invention, when having a labeling substance introduced therein, is usable as a labeled antigen specific to the cancer protein. The specific antibody and the labeled antigen are useful for the diagnosis of and the research on the cancer.

The peptides of the present invention can be produced from readily available commercial amino acids and the like, for example, by usual chemical synthetic processes through a simple and easy procedure. Processes for preparing the peptides of the present invention will be described below in detail.

The peptides of the invention can be prepared by common peptide synthesis processes, such as those described in Schroder and Luhke, "The Peptides," Vol. 1, Academic Press, New York, U.S.A. (1966), or Izumiya et al., "Peptide Synthesis," Maruzen Co. (1975). These processes include the azide process, chloride process, acid anhydride process, mixed acid anhydride process, dicyclohexylcarbodiimide (DCC) process, active ester process (using p-nitrophenyl ester, N-hydroxysuccinic acid imide ester, cyanomethyl ester or the like), process wherein Woodward reagent K is used, carbodiimidazole process, oxidation-reduction process, DCC/additive (N-hydroxybenzotriazole (HOBT), N-hydroxysuccinimide (HOSu)) process, etc. These processes can be practiced by solid-phase or solution method. The peptides of the present invention are synthesized by these processes, for example, by the stepwise method wherein amino acids are coupled one after another to a terminal amino acid by condensation, or by preparing several fragments of amino acid sequence first and coupling the fragments.

More specifically, the solid-phase method, for example, is practiced in the following manner. A C-terminal amino acid, i.e., an amino acid with its amino group protected, is first coupled to an insoluble carrier by its carboxyl group. The insoluble carrier is not limited specifically insofar as it can be coupled to the reactive carboxyl group. Examples of useful carriers are chloromethyl resin, bromomethyl resin and like halogenomethyl resins, phenylacetamido resin, hydroxymethyl resin, phenolic resin, tert-alkyloxycarbonylhydrazide resin, p-methylbenzhydrylamine resin, benzhydrylamine resin, phenylethylamine resin (G. H. Matsuda and J. M. Stewart, Peptides, 45–50, 1981), etc. Subsequently, the amino protective group is removed, and amino-protected amino acids are then successively coupled to the amino acid in accordance with the amino acid sequence of the peptide to be obtained, by the condensation reaction between the reactive amino group and reactive carboxyl group. The amino acids are coupled stepwise to complete the whole sequence. The desired peptide can be obtained by removing the resulting peptide from the insoluble carrier.

It is preferable that amino acids having a sidechain functional group, such as Arg, Tyr, Glu, Thr, Lys, His, Cys and Ser, have their functional group proteted by a usual protective group for use in the foregoing processes. The protective group is removed after the completion of the reaction. The functional groups participating in the reaction is usually activated. These reaction procedures are known, and suitable reagents, etc. are selected from those already known.

Examples of protective groups for the amino group are benzyloxycarbonyl, Boc, tert-amyloxycarbonyl, fluorenylmethoxycarbonyl (Fmoc), 9-fluorenylmethoxycarbonyl, isobornyloxycarbonyl, p-methoxybenzyloxycarbonyl, Cl-Z, adamantyloxycarbonyl, trifluoroacetyl, phthalyl, formyl, o-nitrophenylsulfenyl, diphenylphosphinothioyl, etc.

Examples of protective groups for the carboxyl group are those capable of forming alkyl esters (such as methyl, ethyl, propyl, butyl and tert-butyl esters), Bzl ester, p-nitrobenzyl ester, MeBzl ester, p-chlorobenzyl ester, benzhydryl ester, carbobenzoxyhydrazide, tert-butyloxycarbonylhydrazide, tritylhydrazide, etc.

Examples of protective groups for the guanidino group of Arg are Tos, nitro, benzyloxycarbonyl, amyloxycarbonyl, etc.

The hydroxyl group of Ser and Thr, is protectable, for example, by esterification or etherification, although it need not always be protected. Examples of groups suitable for esterification are lower alkanoyl groups such as acetyl and tert-butylcarbonyl, cyclohexylcarbonyl, benzylcarbonyl, aroyl groups such as benzoyl, groups derived from carbonic acid such as benzoyloxycarbonyl and ethyloxycarbonyl, etc. Examples of groups suitable for etherification are benzyl, tetrahydropyranyl, tert-butyl, etc.

Examples of protective groups for the hydroxyl group of Tyr are Bzl, Cl$_2$Bzl, Br-Z, benzyloxycarbonyl, acetyl, Tos, tert-butyl, etc.

Examples of protective groups for the amino group of Lys are benzyloxycarbonyl, Cl-Z, Cl$_2$Bzl, Boc, Tos, etc.

Examples of protective groups for the imino group of His are Tos, Bzl, etc.

Examples of protective groups for the thiol group of Cys are MeBzl, Bzl, p-methylbenzyl, etc.

The carboxyl group of Glu is protected by being esterified with benzyl alcohol, methaol, ethanol, tert-butanol, etc.

Examples of functional groups participating in the reaction, especially carboxyl groups, as activated are corresponding acid chlorides, acid anhydrides or mixed acid anhydrides, azides, activated esters (esters formed from pentachlorophenol, p-nitrophenol, N-hydroxysuccinimide, N-hydroxybenzotriazole, N-hydroxy-5-norbornene -2,3-dicarboxymide, etc.), etc.

The condensation reaction (peptide linkage forming reaction) between the reactive amino group and reactive carboxyl group can be conducted in the presence of a solvent. The solvents which can be used are those already known for use in forming peptide linkages, such as anhydrous or water-containing dimethylformamide (DMF), dimethylsulfoxide (DMSO), pyridine, chloroform, dioxane, dichloromethane, tetrahydrofuran (THF), ethyl acetate, N-methylpyrrolidone, hexamethylphosphoric triamide (HMPA) and mixtures of such solvents. The ratio between the two starting compounds, which are not limited specifically, is usually 1 to 5 moles, preferably 1 to 1.5 moles, of one of the compounds per mole of the other compound. The reaction temperature is suitably determined from the range which is usually employed for peptide linkage forming reactions. The temperature range is generally from about $-40°$ to about $60°$ C., preferably from about $-20°$ to about $40°$ C. The reaction time is generally several minutes to about 30 hours.

The mixed acid anhydride process is conducted in a suitable solvent in the presence of a basic compound using an alkyl haloformate such as methyl chloroformate, methyl bromoformate, ethyl chloroformate, ethyl bromoformate or isobutyl chloroformate. Examples of useful basic compounds are organic bases such as triethylamine, trimethylamine, pyridine, dimethylaniline, N-methyl-morpholine, 1,5-diazabicyclo[4,3,0]nonene-5 (DBN), 1,5-diazabicyclo[5,4,0]undecene-5 (DBU) and 1,4-diazabicyclo-[2,2,2]octane (DABCO), and inorganic bases such as potassium carbonate, sodium carbonate, potassium hydrogencarbonate and sodium hydrogencarbonate. Examples of useful solvents are those conventionally used for the mixed acid anhydride process and including halogenated hydrocarbon such as methylene chloride, chloroform and dichloroethane, aromatic hydrocarbons such as benzene, toluene and xylene, ethers such as diethyl ether, THF and dimethoxyethane, esters such as methyl acetate and ethyl acetate, aprotic polar solvents such as DMF, DMSO and HMPA, etc. The reaction is conducted usually at $-20°$ to $100°$ C., preferably $-20°$ to $50°$ C. generally for 5 minutes to 10 hours, preferably 5 minutes to 2 hours.

For the azide process, a compound having an azido group is used. Such compound can be prepared, for example, in the following manner. First, a compound having a carboxyl group as activated, for example, by esterification with an alcohol such as methyl alcohol, ethyl alcohol, benzyl alcohol is reacted with a hydrazine hydrate in a suitable solvent. The solvent to be used is, for example, dioxane, DMF, DMSO or a mixture of such solvents. Usually 5 to 20 moles, preferably 5 to 10 moles of the hydrazine hydrate is used per mole of the activated carboxyl. The reaction is conducted usually at a temperature of up to $50°$ C, preferably $-20°$ to $30°$ C. Thus, a compound (hydrazide) can be obtained which contains hydrazino group substituted for the alkoxy moiety of the ester. The hydrazide is then converted to an azide compound by reacting the derivative with a nitrous acid compound in a suitable solvent in the presence of an acid. Usually usable for this reaction is hydrochloric acid as the acid, dioxane, DMF, DMSO or a mixture of these solvents as the solvent, and sodium nitrite, isoamyl nitrite, nitrosyl chloride as the nitrous acid compound. The nitrous acid compound is used usually in an amount of 1 to 2 moles, preferably 1 to 1.5 moles, per mole of the hydrazine derivative. The reaction is conducted usually at $-20°$ to $0°$ C, preferably $-20°$ to $-10°$ C. generally for about 5 to about 10 minutes.

The peptide linkage forming reaction can be conducted also in the presence of a condensation agent such as dicyclohexylcarbodiimide (DCC), carbodiimidazole or like carbodiimide reagent, tetraethylpyrophosphine or the like.

When the protective groups should be removed in the foregoing reactions and in the final step, the group is removed by a usual method. Examples of such methods are reduction methods such as hydrogenation with use of palladium, palladium black or like catalyst and reduction using metallic sodium in liquid ammonia, acidolysis with a strong acid such as trifluoroacetic acid (TFA), hydrochloric acid, hydrofluoric acid, methanesulfonic acid or hydrobromic acid, etc. Hydrogenation using the catalyst can be conducted, for example, at a hydrogen pressure of 1 atm. at $0°$ to $40°$ C. Usually about 100 mg to about 1 g of the catalyst is used. Generally, the reaction takes about 1 to about 48 hours. The acidolysis is carried out without using any solvent usually at about $0°$ to about $30°$ C., preferably about $0°$ to about $20°$ C., for about 15 minutes to about 1 hour. The acid is used usually in about 5 to about 10 times the amount of the compound to be treated. When the amino protective group only is to be removed by acidolysis, it is desirable to use trifluoroacetic acid or hydrochloric acid as the acid. Reduction using metallic sodium in liquid ammonia can be conducted using metallic sodium in such an amount that the reaction mixture remains colored permanent blue for about 30 seconds to about 10 minutes. The reaction can be conducted usually at about $-40°$ C. to about $-70°$ C.

The peptide of the present invention thus prepared is isolated and purified by a conventional method, for example, by extraction, distribution, column chromatography or the like.

Into the peptide thus obtained may be introduced a radioactive substance such as $^{125}$I or $^{131}$I, or an enzymatic reagent such as peroxidase (POX), procarboxypeptidase, glyceroaldehyde-3-phosphoric acid dehydrogenase, amylase, phosphorylase, D-Nase, R-Nase, $\beta$-galactosidase, glucose-6-phosphate dehydrogenase, ornithine decarboxylase or the like. The peptide is then usable as a labeled antigen for use in radioimmunoassay or enzymeimmunoassay. The radioactive substance can be introduced into the peptide by usual methods. The radioactive iodine can be applied, for example, by the oxidative iodination method using Chloramine T (see W. M. Hunter and F. C. Greenwood, Nature, 194, 495 (1962) and Biochem. J. 89, 144 (1963)). The enzymatic reagent can be introduced by usual known methods, for example, by the method of B. F. Erlanger et al. (Acta. Endocrinol. Suppl., 168, 206 (1972)) and the method of M. H. Karol et al. (Proc. Natl. Acad. Sci., U.S.A., 57, 713 (1967)).

The above oncogene-related peptide can be used as a hapten for producing an immunogen or antigen. Therefore, this invention provides an antigen or immunogen which comprises an oncogene-related peptide and a carrier, the peptide serving as a hapten and comprising a portion of the amino acid sequence of a gene product coded for by an oncogene A detail description will be given of the process for preparing such immunogen or antigen using the peptide of the invention as a hapten.

The immunogen or antigen is prepared by reacting the peptide of the invention, serving as a hapten, with a suitable carrier in the presence of a hapten-carrier binding reagent. The carriers to be bound to the hapten are a wide variety of natural or synthetic high-molecular-weight proteins which are conventionally used for preparing antigens. Examples of useful carriers are animal serum albumins such as equine serum albumin, bovine serum albumin, rabbit serum albumin, human serum albumin and ovine serum albumin; animal serum globulins such as equine serum globulin, bovine serum globulin, rabbit serum globulin, human serum globulin and ovine serum globulin; animal thyroglobulins such as porcine thyroglobulin, equine thyroglobulin, bovine thyroglobulin rabbit thyroglobulin, human thyroglobulin and ovine thyrogglobin; animal hemoglobin such as equine hemoglobin bovine hemoglobin, rabbit hemoglobin, human hemoglobin and ovine hemoglobin; animal hemocyanins such as keyhole limpet hemocyanin (KLH); proteins extracted from ascaris (ascaris extracts disclosed in Unexamined Japanese Patent Publication No. 56-16414, J. Immun., 111, 260-268 (1973), J. Immun., 98, 893-900 (1967), J. Immun., 122, 302-308 (1979) and Am. J. Physiol., 199, 575-578 (1960), or such extracts as further purified); polylysine, polyglutamic acid, lysine-glutamic acid copolymer, copolymer containing lysine or ornithine, etc.

The hapten-carrier binding reagents to be used are a wide variety of those conventionally used for preparing antigens. More specific examples of such reagents are dehydrating condensation agents including diazonium compounds for crosslinking Tyr, His and Trp, such as bisdiazotized benzidine (BDB) and bisdiazotized 3,3'-dianisidine (BDD); aliphatic dialdehydes for crosslinking amino group with amino group, such as glyoxal, malondialdehyde, glutaraldehyde, succinaldehyde and adipaldehyde; dimaleimide compounds for crosslinking thiol group with thiol group, such as N,N'-o-phenylenedimaleimide and N,N'-m-phenylenedimaleimide; maleimido carboxyl-N-hydroxysuccinimide esters for crosslinking amino group with thiol group, such as m-maleimidobenzoyl-N-hydroxysuccinimide ester (MBS) and 4-(maleimidomethyl)-cyclohexane-1-carboxyl-N'-hydroxysuccinimide ester; reagents for forming an amide linkage between amino group and carboxyl group in usual peptide linkage forming reactions, e.g. carbodiimides such as DCC, N-ethyl-N'-dimethylaminocarbodiimide, 1-ethyl-3-diisopropylaminocarbodiimide and 1-cyclohexyl-3-(2-morpholinyl-4-ethyl)-carbodiimide; etc. Also usable as the hapten-carrier binding reagent is the combination of a diazoniumarylcarboxylic acid, such as p-diazoniumphenylacetic acid, and a usual peptide linkage forming reaction reagent, such as the above-mentioned dehydrating condensation agent.

The reaction for preparing the immunogen is conducted, for example, in an aqueous solution or a usual buffer having a pH of 7 to 10, preferably a buffer having a pH of 8 to 9, at 0° to 40° C., preferably around room temperature. The reaction usually takes about 1 to about 24 hours, preferably 2 to 5 hours. Examples of typical buffers for this reaction are as follows.

0.2N sodium hydroxide-0.2M boric acid-0.2M potassium chloride buffer
0.2M sodium carbonate-0.2M boric acid-0.2M potassium chloride buffer
0.05M sodium tetraborate-0.2M boric acid-0.05M sodium chloride buffer
0.1 M potassium dihydrogenphosphate-0.05M sodium tetraborate buffer While the proportions of the hapten, the hapten-carrier binding reagent and the carrier can be determined suitably, it is desirable to use the carrier in about 1 to 6 times, preferably about 1 to about 5 times, the amount by weight of the hapten and to use about 1 to about 10 moles of the reagent per mole of the hapten. The reaction affords the desired immunogen in the form of a peptide-carrier complex wherein the hapten is bound to the carrier with the reagent in between.

The immunogen or antigen resulting from the reaction is readily isolated and purified by a usual method such as dialysis, gel filtration, fractional precipitation or the like.

This invention also provides an antibody against the above immunogen or antigen. Such antibody can be produced with use of the immunogen or antigen as prepared above, by giving the immunogen or antigen to mammal to cause the animal to produce the desired antibody in vivo and collecting the antibody.

The mammal to be used for the production of antibodies, although not limited specifically, is preferably rabbit or guinea pig. The antibody is produced by diluting a predetermined amount of the antigen with physiological saline to a suitable concentration, admixing the dilution with complete Freund's adjuvant to obtain a suspension and administering the suspension to a mammal. For example, a rabbit can be immunized by subcutaneously injecting the suspension (at a dose of 0.1 to 5 mg at a time calculated as the amount of the antigen) and thereafter repeating the injection every two weeks for 2 to 10 months, preferably for 4 to 6 months. The antibody is obtained by collecting the blood from the immunized animal one to 2 weeks after the last injection, centrifuging the blood and separating the serum.

The desired antibody can be produced also by fusing plasmacytes of the mammal immunized as above with plasmacytoma cells, cloning the fusion cells producing the desired monoclonal antibody and collecting the monoclonal antibody from the resulting clone culture in the conventional manner.

The mammal to be immunized for producing the monoclonal antibody is suitably selected in view of the compatibility with the plasmacyoma cells to be used for fusion. Generally mouse and rat are used. The basic procedures, means, etc. for the fusion and other processes may be those already known, for example, those used in the method of Milstein et al. (Method in Enzymology, vol. 73, p 3 (1981)).

In this way, the desired antibody can be obtained which has outstanding specificity to the immunogen used. The antibody is useful for RIA (radioimmunoassay), EIA (enzymeimmunoassay), luminescence immunoassay, etc. for determining the corresponding cancer protein and for staining tissues.

Therefore, the present invention also provides a method of determining a gene product coded for by an oncogene characterized in that the gene product is determined by an immunoreaction with use of the foregoing antibody of the invention. Typically, the method comprises the steps of reacting the gene product in a sample with a predetermined amount of a labelled antibody prepared by labelling the above antibody of the invention, and measuring the labelled antibody consumed for the reaction or the amount of the unreacted labelled antibody.

The present invention will be described below in greater detail with reference to examples for preparing peptides of the present invention, examples for preparing immunogen from the peptides and examples for preparing antibodies from the immunogens. However, the invention is not limited to these examples.

<PREPARATION OF PEPTIDES>

PREPARATION EXAMPLE 1

Preparation of HPV 18 (E6) (148-158)

Figure 1:
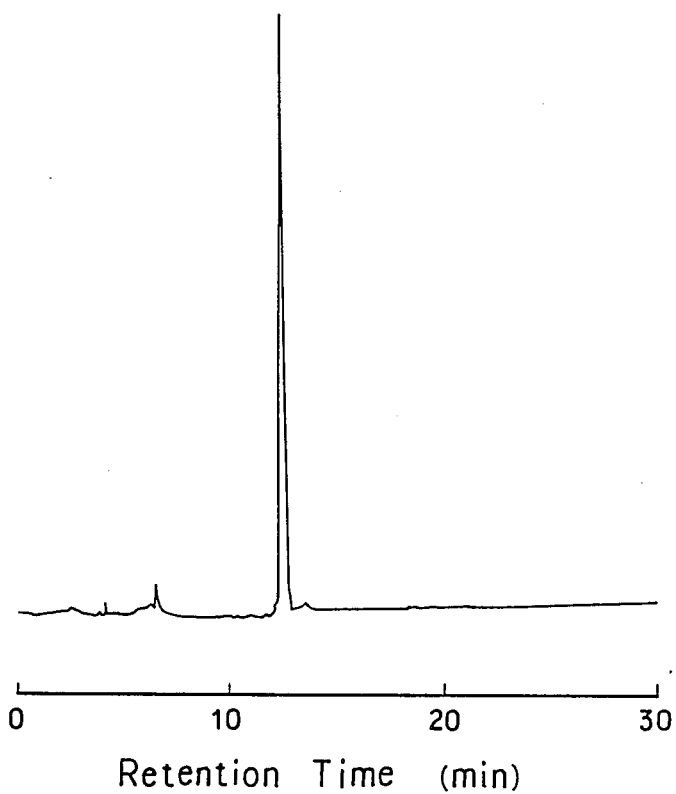
FIGS. 1 to 17 show the results of HPLC analysis on the peptides of the invention obtained in Preparation Examples 1 to 17.

The above peptide was synthesized using a peptide synthesizer, Model 430A, product of Applied Biosystems.

The starting resin used was Boc-Leu-4-OCH$_2$-Pam resin (1% divinylbenzene-crosslinked polystyrene, 0.5 mmol-Boc-Leu, 0.82 mmol/g, Pam=phenylacetamidmethyl). Each of the following amino acid derivatives were successively introduced into the starting material first at the C terminal according to the program listed in Table 1 below using the synthesizer comprising an activator vessel, a concentrator vessel and a reaction vessel as shown in Table 1 below. While the symmetric acid anhydride process was resorted to for the condensation reaction, an active ester of 1-hydroxybenzotriazole (HOBT) was used for the introduction of Boc-Arg(Tos), as well as of Boc-Gln-.

Boc-Gln
Boc-Thr(Bzl)
Boc-Glu(OBzl)
Boc-Arg(Tos)
Boc-Arg(Tos)
Boc-Thr(Bzl)
Boc-Arg(Tos)
Boc-Ser(Bzl)
Boc-Ser(Bzl)
Boc-Arg(Tos).

TABLE 1

Activator vessel (1) Preparation of symmetric anhydride or active ester of
Boc-amino acid derivative

| | |
|---|---|
| Boc-amino acid derivative | 2 mmols |
| DCC | 1 mmol |

Stirring in DMF-CH$_2$Cl$_2$ for 5 to 6 min
Or
Boc-amino acid derivative

| | |
|---|---|
| (Gln or Arg(Tos)) | 2 mmols |
| DCC | 2 mmols |
| HOBT | 2 mmols |

Stirring in DMF-CH$_2$Cl$_2$ for 15 to 25 min,
followed by
removal of insolubles and
transfer to the
concentrator vessel Concentrator vessel (2) Filtration, concentration under nitrogen gas for 12 to 16 min, and replacement of the solvent CH$_2$Cl$_2$ by DMF Reaction vessel (3) Removal of Boc with 60% TFA/CH$_2$Cl$_2$ for 15 to 20 min
(4) Washing with CH$_2$Cl$_2$ (3 times)
(5) Neutralization with diisopropylethylamine (2 times)
(6) Washing with DMF (6 to 8 times)
(7) Coupling reaction
Stirring for 60 min (2 times for Boc-Gln or Boc-Arg(Tos))
(8) Washing with DMF (3 times) and with CH$_2$Cl$_2$ (6 times)

The peptide chain was successively elongated according to the above program. The protected peptide resin resulting from the final coupling reaction was treated with HF in the presence of anisole at 0° C. for 1 hour to remove the protective group and the resin, followed by washing with ethyl acetate, drying, extraction with 1M acetic acid and lyophilizing to obtain the desired peptide.

Yield:
Protected peptide resin: 1.38 g
Crude peptide: 300 mg

Subsequently, the crude peptide was purified by HPLC under the following conditions.

Column: YMC Pack D-ODS-5 (2.1×25 cm, Yamamura Chemical Laboratories Co., Ltd.)
Eluent: 0.01N HCl/CH$_3$CN=95/5→80/20 (30 min)
Detection: 210 nm
Flow rate: 10 ml/min Consequently, 158.7 mg of a purified peptide was obtained (yield 52.9% based on the crude peptide).

The peptide, HPV 18 (E6) (448-158) obtained had the following properties.

Rf values
Rf$^1$=0.00 (n-butanol:acetic acid:water=4:1:5, upper phase)
Rf$^2$=0.07 (n-butanol:pyridine:acetic acid:water=30:20:6:24)

In the following examples, the Rf$^1$ and Rf$_2$ values were determined using the same solvent mixtures as above.

Analysis by HPLC

FIG. 1 shows the result of HPLC (eluent 0.01N HCl/CH$_3$CN=95/5→75/5, 30 min, detection 210 nm, flow rate 1.0 ml/min) using TSK-Gel ODS-120T (0.46×25 cm, Toyo Soda Co.)

Amino acid analysis values: (as determined by amino acid analyzer, Model Hitachi 835)

| Amino acid | Value | Amino acid | Value |
| --- | --- | --- | --- |
| Thr(2) | 2.01 | Ser(2) | 1.78 |
| Glu(2) | 2.12 | Leu(1) | 1.08 |
| Arg(4) | 4.03 | | |

The analysis values were determined after hydrolyzing the peptide with 6N hydrochloric acid (at 110° C. for 24 hours). This procedure was followed also in the following examples unless otherwise specified.

Optical rotation: $[\alpha]_D^{22.5} = -43.7°$ (c=0.1, 1M acetic acid)

PREPARATION EXAMPLE 2

Preparation of hst (169–187)

The starting resin used was Boc-Thr(Bzl)-4-OCH$_2$-Pam resin (1% divinylbenzene-crosslinked polystyrene, 0.5 mmol-Boc-Thr(Bzl), 0.73 mmol/g). Each of the amino acid derivatives listed below were successively introduced into the starting material first at the C-terminal following the general procedure of Preparation Example 1. The coupling reaction was conducted for 20 to 25 minutes for the symmetic acid anhydride process or for 40 minutes (2 times) for the active ester process.

Boc-Lys (Cl-Z)
Boc-Gly
Boc-Asn
Boc-Lys (Cl-Z)
Boc-Ser(Bzl)
Boc-Leu
Boc-Ala
Boc-Ile
Boc-Phe
Boc-Met
Boc-Gly
Boc-Pro
Boc-Tyr(Br-Z)
Boc-Lys(Cl-Z)
Boc-Tyr(Br-Z)
Boc-Ser(Bzl)
Boc-Glu(OBzl)
Boc-Tyr(Br-Z)

The protected peptide resin resulting from the final coupling reaction was treated in the same manner as in Preparation Example 1 to obtain the desired peptide in a crude form.

Yield
  Protected peptide resin: 1.62 g
  Crude peptide: 750 mg

Figure 2:
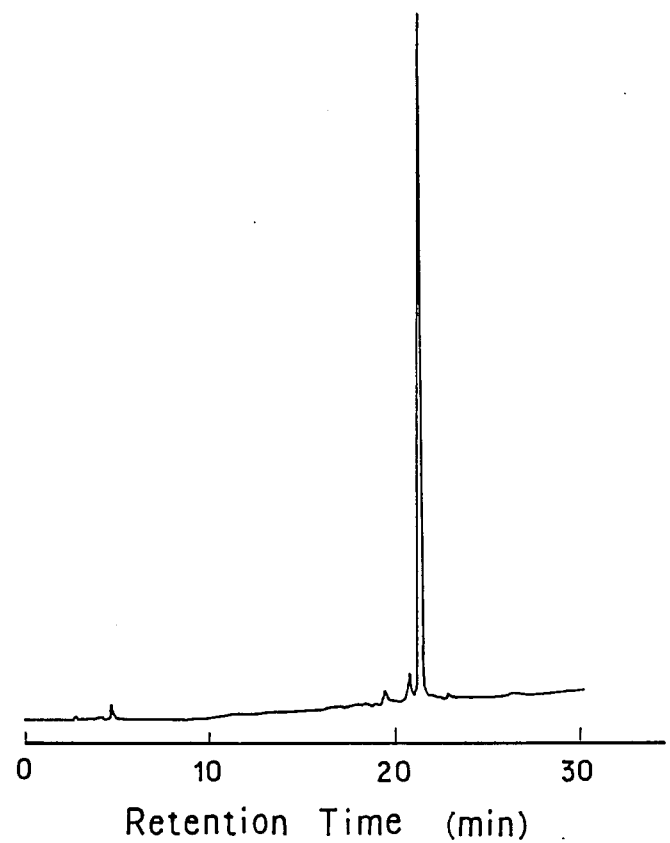

Subsequently, the crude peptide was puified by HPLC under the following conditions.
Column: TSK-Gel ODS-120T (21.5×300 mm)
Eluent: 0.01N HCl/CH$_3$CN=70/30→50/50 (30 min)
Detection: 210 nm
Flow rate: 10 ml/min Consequently, 50 mg of a purified peptide was obtained (yield 25.0% based on the crude peptide).
The peptide had the following properties.
Rf values
  Rf$^1$=0.03
  Rf$^2$=0.35
Analysis by HPLC
FIG. 2 shows the result of HPLC (eluent 0.01N HCl/CH$_3$CN=85/15→55/45, 30 min, detection 214 nm, flow rate 1.0 ml/min) using TSK-Gel ODS-120T (0.46×25 cm).

Amino acid analysis values: (as determined by the same analyzer as above)

| Amino acid | Value | Amino acid | Value |
| --- | --- | --- | --- |
| Asp(1) | 1.18 | Thr(1) | 1.09 |
| Ser(2) | 1.81 | Glu(1) | 1.25 |
| Gly(2) | 2.20 | Ala(1) | 1.02 |
| Met(1) | 0.95 | Ile(1) | 0.99 |
| Leu(1) | 1.08 | Tyr(3) | 2.92 |
| Phe(1) | 1.00 | Lys(3) | 2.50 |

Optical rotation $[\alpha]_D^{24} = -52.3°$ (c=1, 1M acetic acid)

PREPARATION EXAMPLE 3

Preparation of hst (108–133)

The starting resin used was Boc-Ser(Bzl)-4-OCH$_2$-Pam resin (1% divinylbenzene-crosslinked polystyrene, 0.5 mmol-Boc-Ser(Bzl), 0.78 mmol/g). Each of the amino acid derivatives listed below were successively introduced into the starting material first at the C terminal following the general procedure of Preparation Example 1.

Boc-Ala
Boc-Val
Boc-Gly
Boc-Phe
Boc-Ile
Boc-Ser(Bzl)
Boc-Val
Boc-Val
Boc-Gly
Boc-Arg(Tos)
Boc-Glu(OBzl)
Boc-Val
Boc-Pro
Boc-Ser(Bzl)
Boc-Leu
Boc-Glu(OBzl)
Boc-Leu
Boc-Leu
Boc-Ser(Bzl)
Boc-Asp(OcHex)
Boc-Arg(Tos)
Boc-Thr(Bzl)
Boc-Asp(OcHex)
Boc-Ala
Boc-His(Tos)

The protected peptide resin resulting from the final coupling reaction was treated in the same manner as in Preparation Example 1 (HF treatment in the presence of anisole at −20° C. for 30 minutes and then at 0° C. for 30 minutes) to obtain the desired peptide in a crude form.

Yield
  Protected peptide resin: 1.50 g
  Crude peptide: 260 mg (1.00 g of the resin, HF treatment)

Figure 3:
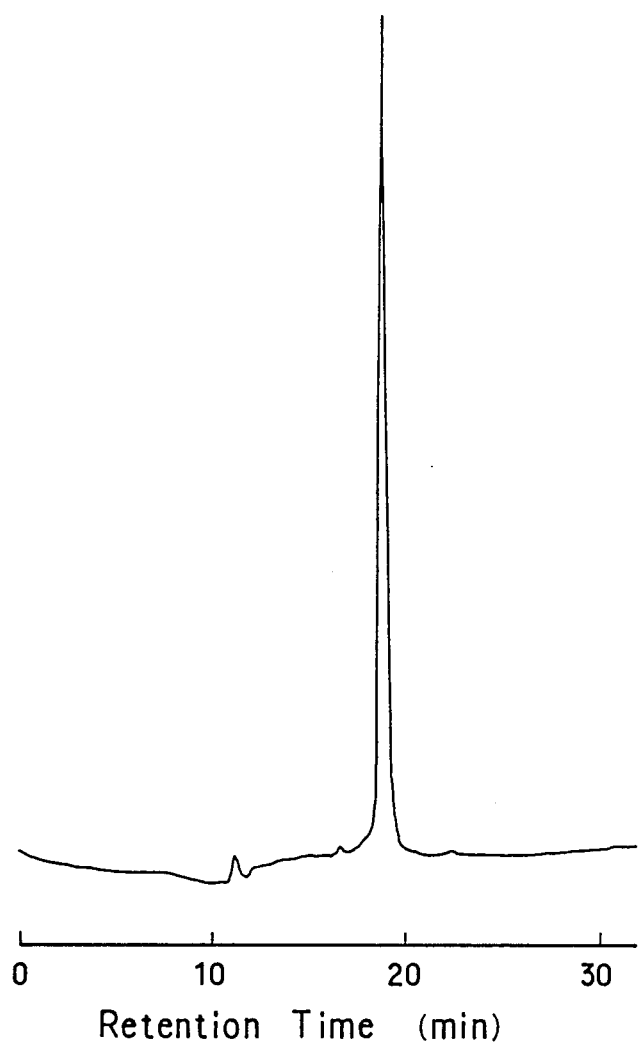

The crude peptide was subsequently purified by HPLC under the following conditions.
Column: YMC Pack D-ODS-5 (2.1×25 cm)
Eluent: 0.01N HCl/CH$_3$CN=70/30→50/50 (30 min)
Detection: 210 nm
Flow rate: 10 ml/min Consequently, 116.3 mg of a purified peptide was obtained (yield 44.7% based on the crude peptide).
The peptide had the following properties.
Rf values Rf¹=0.04
Rf²=0.35
Analysis by HPLC
FIG. 3 shows the result of HPLC (eluent 0.01N HCl/CH₃CN=75/25→50/50, 30 min, detection 210 nm, flow rate 10 ml/min) using TSK-Gel ODS-120T (2.1×30 cm).
Amino acid analysis values: (110° C., 24 hours)

| Amino acid | Value | Amino acid | Value |
| --- | --- | --- | --- |
| Asp(2) | 1.70 | Thr(1) | 0.94 |
| Ser(4) | 3.59 | Glu(2) | 1.99 |
| Pro(1) | 1.10 | Gly(2) | 2.14 |
| Ala(2) | 2.06 | Val(4) | 3.47 |
| Ile(1) | 1.02 | Leu(3) | 3.05 |
| Phe(1) | 1.00 | His(1) | 0.95 |
| Arg(2) | 2.05 | | |

Amino acid analysis values: (110° C., 48 hours)

| Amino acid | Value | Amino acid | Value |
| --- | --- | --- | --- |
| Asp(2) | 1.72 | Thr(1) | 0.86 |
| Ser(4) | 3.04 | Glu(2) | 1.98 |
| Pro(1) | 1.31 | Gly(2) | 2.12 |
| Ala(2) | 2.05 | Val(4) | 3.93 |
| Ile(1) | 1.01 | Leu(3) | 2.96 |
| Phe(1) | 0.98 | His(1) | 0.96 |
| Arg(2) | 1.98 | | |

Optical rotation $[\alpha]_D^{24} = -84.7°$ (c=0.1, 1M acetic acid)

PREPARATION EXAMPLE 4

Preparation of ras-gene-product (10–18)

The starting resin used was Boc-Ser(Bzl)-4-OCH₂-Pam resin (1% divinylbenzene-crosslinked polystyrene, 0.5 mmol-Boc-Ser(Bzl), 0.78 mmol/g). The amino acid derivatives listed below were successively introduced into the starting material first at the C terminal following the general procedure of Preparation Example 1 with the exception that the coupling reaction was conducted for 20 to 25 minutes.

Boc-Lys (Cl-Z)
Boc-Gly
Boc-Val
Boc-Gly
Boc-Val
Boc-Ala
Boc-Gly
Boc-Tyr(Br-Z)

The protected peptide resin resulting from the final condensation reaction was treated in the same manner as in Preparation Example 1 to obtain the desired peptide in a crude state.

Yield
Protected peptide resin: 760 mg
Crude peptide: 220 mg

The crude peptide was subsequently purified by HPLC under the following conditions.
Column: YMC Pack D-ODS-5 (2.1×25 cm)
Eluent: 0.01N HCl/CH₃CN=95/5→75/25 (30 min)
Detection: 210 nm
Flow rate: 10 ml/min Consequently, 98.0 mg of a purified peptide was obtained (yield 44.5% based on the crude peptide).

Figure 4:
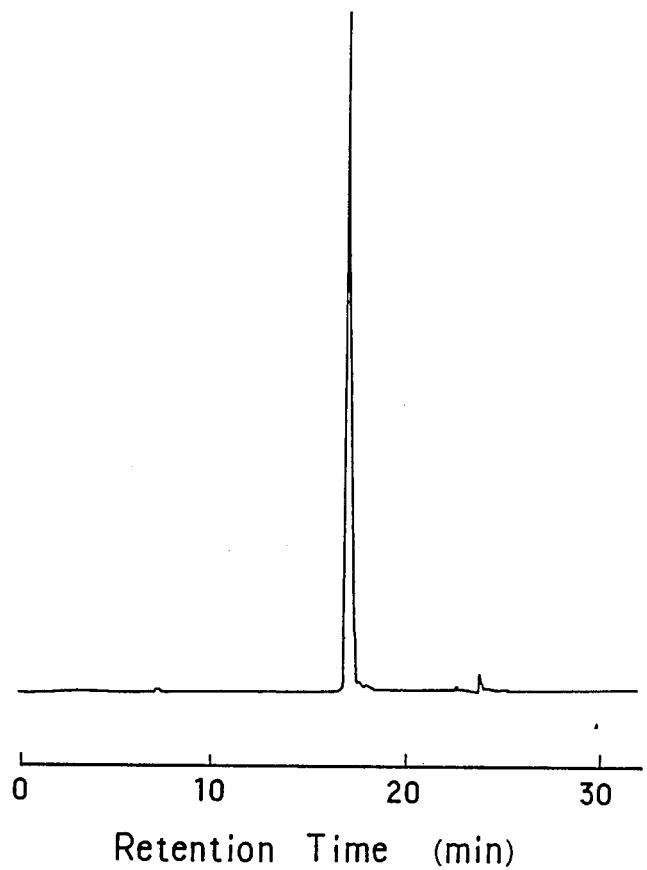

The peptide had the following properties.
Rf values
Rf¹=0.22
Rf²=0.35
Analysis by HPLC
FIG. 4 shows the rsult of HPLC (eluent 0.01N HCl/CH₃CN=95/5→75/25, 30 min, detection 210 nm, flow rate 1.0 ml/min) using TSK-Gel ODS-120T (0.46×25 cm).
Amino acid analysis values

| Amino acid | Value | Amino acid | Value |
| --- | --- | --- | --- |
| Ser(1) | 0.87 | Gly(3) | 3.05 |
| Ala(1) | 0.99 | Val(2) | 2.08 |
| Tyr(1) | 0.95 | Lys(1) | 0.93 |

Optical rotation
$[\alpha]_D^{22.5} = -8.3°$ (c=0.1, 50% acetic acid)

PREPARATION EXAMPLE 5

Preparation of N-ras (41–50)

The above peptide was synthesized using a Beckman system 990 synthesizer.

First, 4.16 g (12.8 mmols) of Boc-Thr(Bzl)-OH was dissolved in 83.0 ml (12.8 mmols) of 0.154M KO-tBu/DMSO solution. To the resulting solution was added 5.0 g (6.4 mmols) of chloromethyl resin (2% divinyl-benzene-crosslinked polystyrene, 200–400 mesh, Cl content 1.28 meq/g). The mixture was reacted at 80° C. for 30 minutes and then at room temperature for 1 hour. The resin was filtered off by suction, washed with ethanol 10 times and dried (yield 6.61 g).

A 10-mg portion of the Boc-Thr(Bzl)-resin thus prepared was treated with 0.5 ml of 6N HCl and 0.5 ml of propionic acid at 130° C. for 2 hours and subjected to amino acid analysis.

The resin was found to have a Thr content of 0.70 mmol per gram of the resin.

Using 3.0 g (0.70 mmol/g) of the Boc-Thr(Bzl)-OCH₂ resin as a starting material, the following Boc-amino acid derivatives were successively introduced into the starting material first at the C terminal according to the program shown in Table 2 below.

Boc-Thr(Bzl)
Boc-Glu(OBzl)
Boc-Gly
Boc-Asp(OBzl)
Boc-Ile
Boc-Val
Boc-Val
Boc-Gln
Boc-Lys(Cl-Z)
Boc-Arg(Tos)

For the coupling reaction, 1.52 g of DCC (7.35 mmols, or about 1.2 times the quantity of each Boc-amino acid derivative, i.e. 14.7 ml calculated as 0.5M DCC/CH₂Cl₂) and 6.3 mmols of the Boc-amino acid derivative were used for 3.0 g of Boc-Thr(Bzl)-OCH₂ resin.

From the Boc-Thr(Bzl) coupled to the resin, the Boc was removed with use of 50% TFA/CH₂Cl₂. The resin was then washed with CH₂Cl₂, thereafter neutralized with 10% triethylamine (TEA)/CH₂Cl₂ and further washed with CH₂Cl₂. The Boc-amino acid derivative was coupled to the resin by the DCC process for condensation, and the condensation was repeated until the reaction was completed. The introduction of Boc-Gln was conducted in the presence of HOBT.

TABLE 2

Solid-phase synthesis program

| Step | Reagents and operations | | Mixing time (min) |
|---|---|---|---|
| 1 | CH$_2$Cl$_2$ | (X3) | 1.5 |
| 2 | TFA (50% in CH$_2$Cl$_2$) | (X1) | 1.5 |
| 3 | TFA (50% in CH$_2$Cl$_2$) | (X1) | 30 |
| 4 | CH$_2$Cl$_2$ | (X6) | 1.5 |
| 5 | TEA (10% in CH$_2$Cl$_2$) | (X3) | 1.5 |
| 6 | CH$_2$Cl$_2$ | (X6) | 1.5 |
| 7 | Boc-amino acid derivative (in CH$_2$Cl$_2$ or DMF) | (X1) | 5 |
| 8 | DCC | (X1) | 120 |
| 9 | CH$_2$Cl$_2$ | (X6) | 1.5 |
| | Repeated coupling | | |
| 10 | CH$_2$Cl$_2$ | (X3) | 1.5 |
| 11 | TEA (10% in CH$_2$Cl$_2$) | (X3) | 1.5 |
| 12 | CH$_2$Cl$_2$ | (X6) | 1.5 |
| 13 | Boc-amino acid derivative and 1-hydroxybenzotriazole | (X1) | 5 |
| 14 | DCC | (X1) | 120 |
| 15 | CH$_2$Cl$_2$ | (X6) | 1.5 |

The protected peptide resin resulting from the final coupling reaction was treated with HF in the presence of anisole at −20° C. for 30 minutes and then at 0° C. for 30 minutes to remove the protective group and the resin, followed by washing with ethyl acetate, drying, extraction with 1M acetic acid and freeze-drying, giving the desired peptide in a crude form.

Yield
  Protected peptide resin: 4.31 g
  After treatment with HF,
  Crude peptide: 240 mg (from 2.0 g of the resin)

Subsequently, the crude peptide was dissolved in 1M acetic acid and subjected to gel filtration using Sephadex G-10 (3.0×140 cm), affording 22.3 mg of a main fraction and 150.6 mg of a side fraction. These fractions were purified by HPLC under the following conditions.
Column: TSK-Gel ODS-120T (21.5×300 mm)
Eluent: 0.01N HCl/CH$_3$CN=85/15→70/30 (30 min)
Detection: 210 nm
Flow rate: 10 ml/min Consequently, 36.9 mg of a purified peptide was obtained (yield 15.4% based on the crude peptide).

Figure 5:
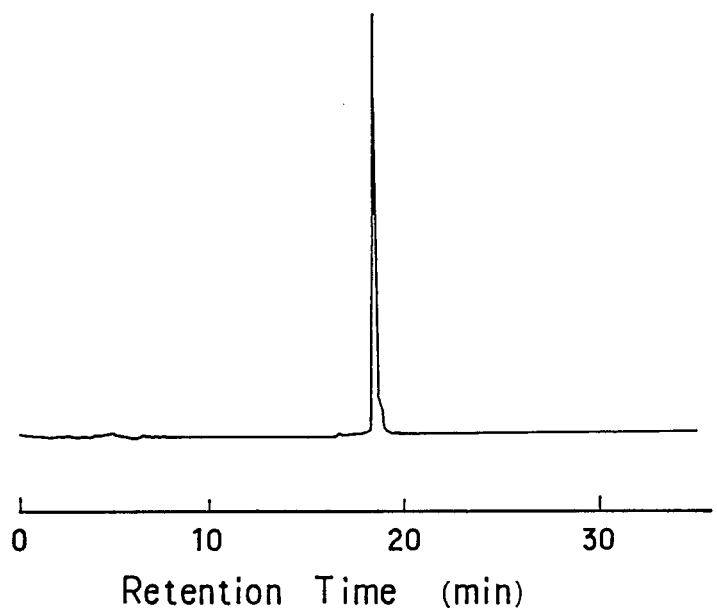

The peptide had the following properties.
Rf values
  Rf$^1$=0.00
  Rf$^2$=0.30
Analysis by HPLC FIG. 5 shows the result of HPLC (eluent 0.01N HCl/CH$_3$CN=90/10→70/30, 30 min, detection 210 nm, flow rate 1.0 ml/min) using TSK-Gel ODS-120T (0.46×25 cm).

Amino acid analysis values

| Amino acid | Value | Amino acid | Value |
|---|---|---|---|
| Asp(1) | 1.00 | Thr(1) | 0.95 |
| Glu(2) | 2.00 | Gly(1) | 1.02 |
| Val(2) | 1.34 | Ile(1) | 0.92 |
| Lys(1) | 1.05 | Arg(1) | 1.01 |

Optical rotation [α]$_D^{22}$=−82.7°(c=0.1, 1M acetic acid)

PREPARATION EXAMPLE 6

Preparation of c-myc (423–437)

Following the general procedure of Preparation Example 5, 3.96 g (13.4 mmols) of Boc-Ser(Bzl)-OH was introduced into 5.0 g (6.4 mmols) of the same chloromethyl resin. Amino acid analysis revealed that the resulting resin contained 0.523 mmol of Ser per gram of the resin.

The Boc-Ser(Bzl)-OCH$_2$ resin (5.0 g) was used, as a starting resin. The Boc amino acid derivatives listed below were successively introduced into the starting material following the general procedure of Preparation Example 5 and using 1.62 g of DCC (9.81 mmols, i.e. 19.6 ml calculated as 0.5M DCC/CH$_2$Cl$_2$) and 9.81 mmols of each amino acid derivative, whereby the peptide chain was elongated.

Boc-Ser(Bzl)
Boc-Asn
Boc-Arg(Tos)
Boc-Leu
Boc-Gln
Boc-Glu(OBzl)
Boc-Leu
Boc-Lys
Boc-His(Tos)
Boc-Lys
Boc-Leu
Boc-Gln
Boc-Glu(OBzl)
Boc-Arg(Tos)
Boc-Arg(Tos)

The protected peptide resin resulting from the final condensation reaction was similarly treated with HF (in the presence of anisole at 0° C. for 1 hour), followed by washing with ethyl acetate, drying, extraction with acetic acid and freeze-drying, giving the desired peptide in a crude form.

Yield
  Protected peptide resin: 11.14 g
  Crude peptide: 298.3 mg (from 880 mg of the resin)

Subsequently, the crude peptide (257.7 mg) was dissolved in 10 ml of 1M acetic acid, and the solution was subjected to gel filtration using Sephadex G-10 (3.0×140 cm) to obtain 235 mg of a main fraction.

The fraction was subsequently purified by HPLC under the following conditions.
Column: TSK-Gel ODS-120T (2.1×30 cm)
Eluent: 0.01N HCl/CH$_3$CN=85/15→60/40 (30 min)
Detection: 210 nm
Flow rate: 10 ml/min Consequently, 100 mg of a purified peptide was obtained (yield 33.5% based on the crude peptide).

Figure 6:
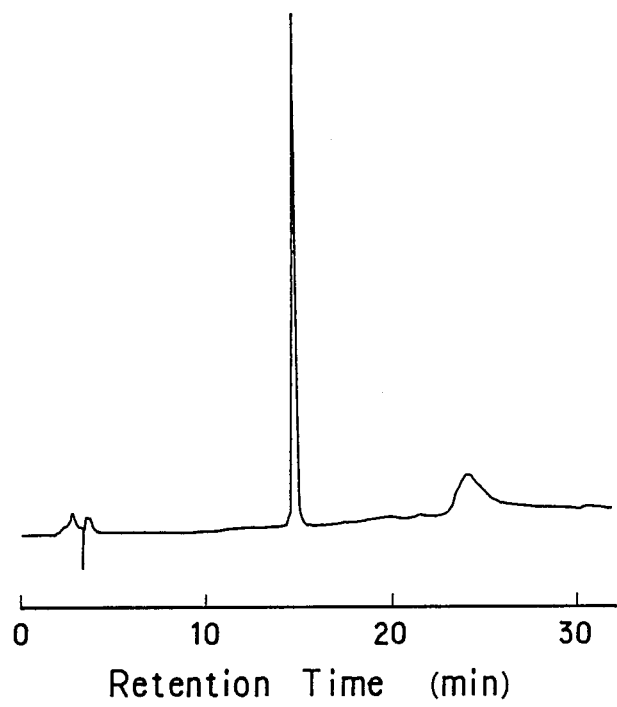

The peptide had the following properties.
Rf values:
  Rf$^1$=0.00
  Rf$^2$=0.30
Analysis by HPLC:

FIG. 6 shows the result of HPLC (eluent 0.01N HCl/CH$_3$CN=90/10→60/40, 30 min, detection 210 nm, flow rate 1.0 ml/min) using TSK-Gel ODS-120T (0.46×25 cm).

Amino acid analysis values:

| Amino acid | Value | Amino acid | Value |
|---|---|---|---|
| Asp(1) | 1.03 | Ser(1) | 0.97 |
| Glu(4) | 3.96 | Leu(3) | 2.99 |
| Lys(2) | 2.09 | His(1) | 1.12 |
| Arg(3) | 2.80 | | |

Optical rotation: [α]$_D^{23}$=−78.7° (c=0.1, 1M acetic acid)

Preparation Example 7

Preparation of c-myc (399–437)

Following the general procedure of Preparation Example 5, 3.96 g (13.4 mmols) of Boc-Ser(Bzl)-OH was introduced into 5.0 g (6.4 mmols) of the same chloromethyl resin. Amino acid analysis revealed that the resulting resin contained 0.523 mmol of Ser per gram of the resin.

The Boc-Ser(Bzl)-OCH$_2$ resin (5.0 g) obtained was used as a starting resin. The Boc amino acid derivatives listed below were successively introduced into the starting material following the general procedure of Preparation Example 5 and using 1.62 g of DCC (9.81 mmols, i.e. 19.6 ml calculated as 0.5M DCC/CH$_2$Cl$_2$) and 9.81 mmols of each amino acid derivative, whereby the peptide chain was elongated.

Boc-Ser(Bzl)
Boc-Asn
Boc-Arg(Tos)
Boc-Leu
Boc-Gln
Boc-Glu(OBzl)
Boc-Leu
Boc-Lys(Cl-Z)
Boc-His(Tos)
Boc-Lys(Cl-Z)
Boc-Leu
Boc-Gln
Boc-Glu(OBzl)
Boc-Arg(Tos)
Boc-Arg(Tos)
Boc-Lys(Cl-Z)
Boc-Arg(Tos)
Boc-Leu
Boc-Leu
Boc-Asp(OBzl)
Boc-Glu(OBzl)
Boc-Glu(OBzl)
Boc-Ser(Bzl)
Boc-Ile
Boc-Leu
Boc-Lys(Cl-Z)
Boc-Gln
Boc-Glu(OBzl)
Boc-Glu(OBzl)
Boc-Ala
Boc-Gln
Boc-Val
Boc-Ser(Bzl)
Boc-Leu
Boc-Ile
Boc-Tyr(Cl$_2$Bzl)
Boc-Ala
Boc-Thr(Bzl)
Boc-Ala

The protected peptide resin resulting from the final coupling reaction was similarly treated with anhydrous HF (in the presence of anisole at −60° C. for 1 hour and then at 0° C. for 30 minutes), followed by washing with ethyl acetate, drying, extraction with acetic acid and freeze-drying, giving the desired peptide in a crude form.

Yield:
  Protected peptide resin: 11.44 g
  Crude peptide: 830 mg (from 2.44 g of the resin)

The crude peptide was subsequently purified by HPLC under the following conditions.
Column: TSK-Gel ODS-120T (2.1×30 cm)
Eluent: 0.01N HCl/CH$_3$CN=75/25→50/50 (30 min)
Detection: 210 nm
Flow rate: 10 ml/min Consequently, 300 mg of a purified peptide was obtained (yield 36.1% based on the crude peptide).

Figure 7:
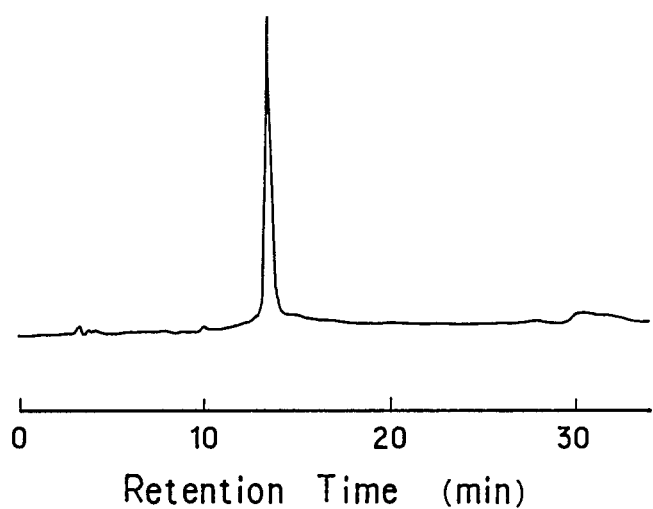

The peptide had the following properties.
Rf values:
  Rf$^1$=0.00
  Rf$^2$=0.30
Analysis by HPLC:
FIG. 7 shows the result of HPLC (eluent 0.01N HCl/CH$_3$CN=80/20→50/50, 30 min, detection 210 nm, flow rate 1.0 ml/min) using TSK-Gel ODS-120T (0.46×25 cm).

Amino acid analysis values:

| Amino acid | Value | Amino acid | Value |
|---|---|---|---|
| Asp(2) | 1.97 | Thr(1) | 0.89 |
| Ser(3) | 2.55 | Glu(10) | 10.66 |
| Ala(3) | 2.86 | Val(1) | 0.92 |
| Ile(2) | 1.95 | Leu(7) | 6.85 |
| Tyr(1) | 1.04 | Lys(4) | 4.03 |
| His(1) | 0.97 | Arg(4) | 3.86 |

Optical rotation: $[\alpha]_D^{24}$ −45.3° (c=0.1, 1M acetic acid)

Preparation Example 8

Preparation of c-myc (420–437)

Following the general procedure of Preparation Example 5, 3.96 g (13.4 mmols) of Boc-Ser(Bzl)-OH was introduced into 5.0 g (6.4 mmols) of the same chloromethyl resin Amino acid analysis revealed that the resulting resin contained 0.523 mmol of Ser per gram of the resin.

The Boc-Ser(Bzl)-OCH$_2$ resin (5.0 g) obtained was used as a starting resin. The Boc amino acid derivatives listed below were successively introduced into the starting material following the general procedure of Preparation Example 5 and using 1.62 g of DCC (9.81 mmols, i.e. 19.6 ml calculated as 0.5M DCC/CH$_2$Cl$_2$) and 9.81 mmols of each amino acid derivative, whereby the peptide chain was elongated.

Boc-Ser(Bzl)
Boc-Asn
Boc-Arg(Tos)
Boc-Leu
Boc-Gln
Boc-Glu(OBzl)
Boc-Leu
Boc-Lys(Cl-Z)
Boc-His(Tos)
Boc-Lys(Cl-Z)
Boc-Leu
Boc-Gln
Boc-Glu(OBzl)
Boc-Arg(Tos)
Boc-Arg(Tos)
Boc-Lys(Cl-Z)
Boc-Arg(Tos)
Boc-Leu

The protected peptide resin resulting from the final coupling reaction was similarly treated with HF (in the presence of anisole at 0° C. for 1 hour), followed by washing with ethyl acetate, drying, extraction with acetic acid and freeze-drying, giving the desired peptide in a crude form.

Yield:
  Protected peptide resin: 11.03 g
  Crude peptide: 257.7 mg (from 700 mg of the resin)

Subsequently, the crude peptide was dissolved in 10 ml of 1M acetic acid, and the solution was subjected to gel filtration using Sephadex G-10 (3.0×140 cm) to obtain 175.3 mg of a main fraction.

The fraction was subsequently purified by HPLC under the following conditions.

Column : TSK-Gel ODS-120T (2.1×30 cm)
Eluent : 0.01N HCl/CH$_3$CN=85/15→60/40 (30 min)
Detection : 210 nm
Flow rate : 10 ml/min Consequently, 100 mg of a purified peptide was obtained (yield 38.8% based on the crude peptide).

The peptide had the following properties.

Rf values:
  Rf$^1$=0.00
  Rf$^2$=0.25

Figure 8:
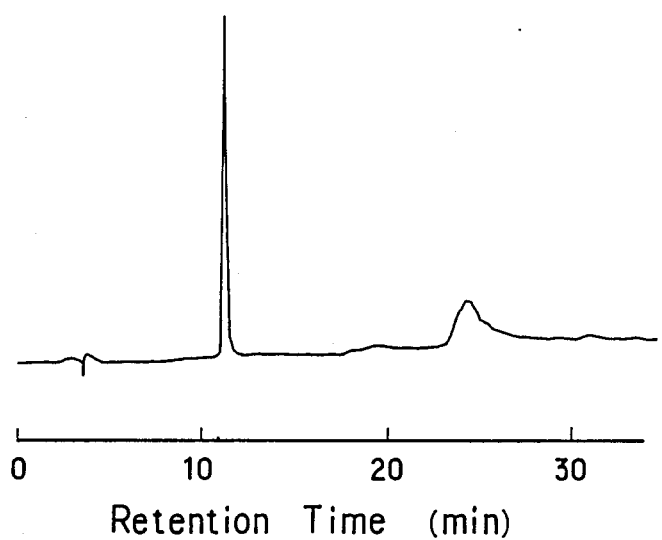

Analysis by HPLC:

FIG. 8 shows the result of HPLC (eluent 0.01N HCl/CH$_3$CN=90/10→60/40, 30 min, detection 210 nm, flow rate 1.0 ml/min) using TSK-Gel ODS-120T (0.46×25 cm).

Amino acid analysis values:

| Amino acid | Value | Amino acid | Value |
| --- | --- | --- | --- |
| Asp(1) | 0.97 | Ser(1) | 0.90 |
| Glu(4) | 3.97 | Leu(4) | 3.80 |
| Lys(3) | 3.04 | His(1) | 1.06 |
| Arg(4) | 4.06 | | |

Optical rotation: $[\alpha]_D^{23.5}=-75°$ (c=0.1, 1M acetic acid)

Preparation Example 9

Preparation of B-lym-1 (44–58)

The peptide was prepared following the general procedure of Preparation Example 8.

Figure 9:
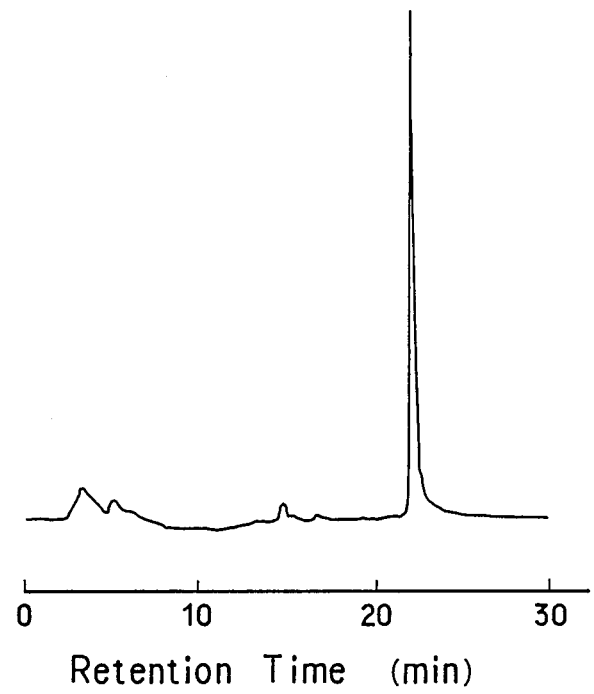

The peptide obtained was analyzed by reversephase HPLC under the following conditions. FIG. 9 shows the result.

Column : Nucleosil 5C$_{18}$ (Chemco Scientific Co., Ltd.) (4.6×250 mm)
Eluent : 0.01N HCl/CH$_3$CN=80/20→60/40 (30 min)
Detection : 214 nm
Flow rate : 1.0 ml/min
Optical Rotation: $[\alpha]_D^{25}=-132.3°$ (c=0.1, 50% acetic acid)
RF values:
  Rf$^1$=0.00
  Rf$^2$=0.51

Preparation Example 10

Preparation of c-myc (244–268)

The peptide was prepared following the general procedure of Preparation Example 8.

Given below are the amino acid analysis values of the peptide obtained.

| Amino acid | Value | Amino acid | Value |
| --- | --- | --- | --- |
| Asp(3) | 3.19 | Thr(3) | 2.97 |
| Ser(4) | 3.70 | Glu(9) | 9.01 |
| Val(3) | 2.55 | Ile(1) | 1.18 |

Figure 10:
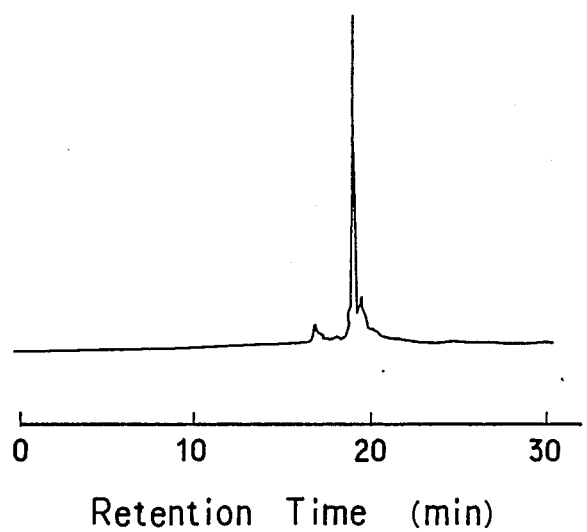

The peptide was analyzed by reverse-phase HPLC under the same conditions as in Preparation Example 9 (except that the eluent used was 0.01N HCl/CH$_3$CN=70/30→50/50 (30 min)). FIG. 10 shows the result.

Preparation Example 11

Preparation of c-myc (11–24)

The peptide was prepared following the general procedure of Preparation Example 8.

Given below are the amino acid analysis values of the peptide obtained.

| Amino acid | Value | Amino acid | Value |
| --- | --- | --- | --- |
| Asp(4) | 4.11 | Ser(1) | 0.89 |
| Glu(1) | 1.02 | Val(1) | 1.01 |
| Leu(1) | 1.02 | Tyr(4) | 3.82 |
| Phe(1) | 1.00 | | |

Figure 11:
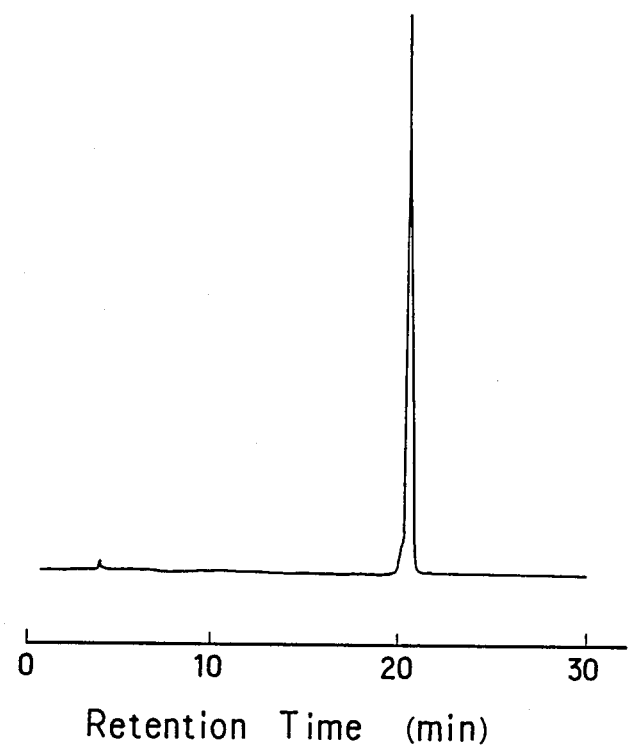

The peptide was analyzed by reverse-phase HPLC under the same conditions as in Preparation Example 9 (except that the eluent used was 0.01N HCl/CH$_3$CN=80/20→55/45 (30 min)). FIG. 11 shows the result.

Preparation Example 12

Preparation of h-TGF-α (33–50)

The starting resin used was Boc-Ala-OCH$_2$-Pam resin (1% divinylbenzene-crosslinked polystyrene, 0.5 mmol Boc-Ala, 0.81 mmol/g). Following the general procedure of Preparation Example 1, the amino acid derivatives listed below were successively introduced into the starting material first at the C-terminal. Generally the coupling reaction was conducted by the symmetric acid anhydride process except for the introduction of Boc-Arg(Tos) which was coupled in the form of an active ester of 1-hydroxybenzotriazole.

| | Position |
| --- | --- |
| Boc-Ala-OH | 9,14 |
| Boc-Arg(Tos)-OH | 10 |
| Boc-Asp(OcHex)-OH | 15 |
| Boc-Cys(4-MeBzl)-OH | 2,11 |
| Boc-Glu(OBzl)-OH | 12 |
| Boc-Gly-OH | 5,8 |
| Boc-His(Tos)-OH | 3,13 |
| Boc-Leu-OH | 16 |
| Boc-Ser(Bzl)-OH | 4,17 |
| Boc-Tyr(2-Br-Z)-OH | 6 |
| Boc-Val-OH | 1,7 |

The protected peptide resin resulting from the final coupling reaction was treated with HF in the presence of anisole at −20° C. for 30 minutes and then at 0° C. for 30 minutes to remove the protective group and the resin. The peptide was further treated with a 1:1 mixture of HF and anisol at 0° C. for 1 hour to remove 4-MeBzl from the Cys residue, washed with ethyl acetate, dried and extracted with 100 ml of 3M acetic acid.

To the extract was added dropwise a solution of 30 mg of potassium ferricyanide in 25 ml of water over 6 hours while maintaining the pH at 6.8 to 7.0 with 10% ammonia water, thereby effecting the cyclization reaction. After the reaction, the reaction mixture was adjusted to a pH of 5.0 with 10% acetic acid, placed on an ion-exchange column (Bio Rad AG 3-X4A, 2.0×3.0 cm, 2.8 meq/g(dry), 100-200 mesh, chloride form) and eluted with water. The resulting eluate was further placed on a column (Bio Rex 70 (2.0×3.0 cm), 10.2 meq/g(dry), 200-400 mesh, sodium form) and eluted first with 5% acetic acid (50 ml) and then with 50% acetic acid (100 ml). The resulting eluate was lyophilized to obtain the desired peptide.

Yield :
  Proteded peptide resin: 1.29 g
  Crude peptide:
    5% acetic acid-eluted fractions=40.9 mg
    50% acetic acid-eluted fractions=115.5 mg The crude peptide (40.9 mg and 115.5 mg) was purified by reverse-phase HPLC under the following conditions.
Column: TSK-Gel ODS-120T (21.5×300 mm)
Eluent: 0.01N HCl/CH$_3$CN=80/20→60/40 (30 min)
Detection : 210 nm
Flow rate : 10 ml/min Consequently, 13.6 mg of a purified peptide was obtained. Yield 8.7% based on the crude peptide, or 1.5% based on the starting resin.

The peptide had the following properties.
Rf values:
  Rf$^1$=0.08
  Rf$^2$=0.00

Figure 12:
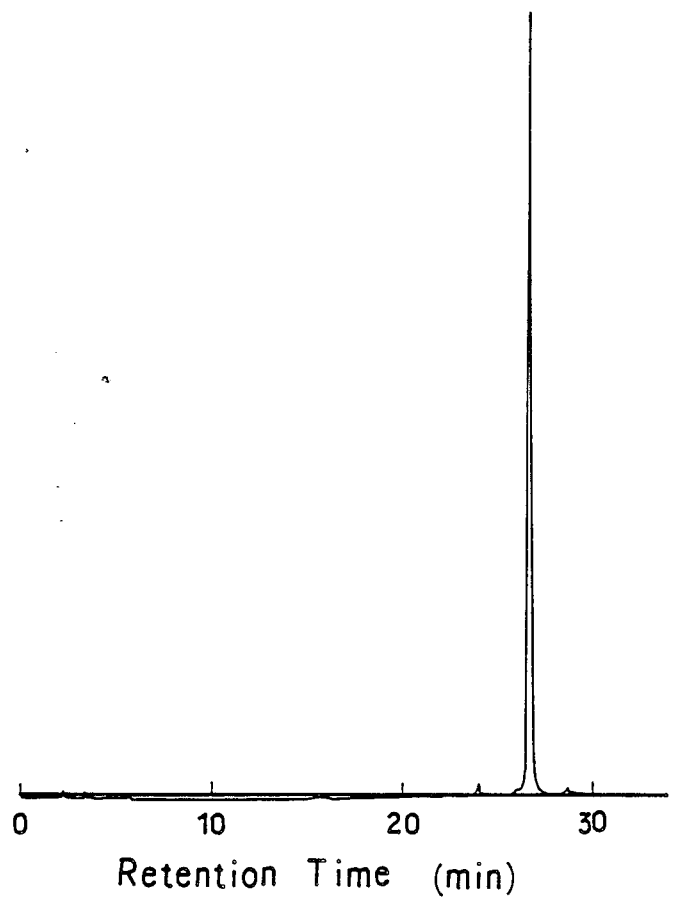

Analysis by HPLC:
FIG. 12 shows the result of HPLC (eluent 0.01N HCl/CH$_3$CN=95/5→75/25, 30 min, detection 210 nm, flow rate 1.0 ml/min) using YMC Pack R-ODS-5 (4.6×25 cm).

Amino acid analysis values:

| Amino acid | Value | Amino acid | Value |
| --- | --- | --- | --- |
| Asp(1) | 1.08 | Ser(1) | 0.93 |
| Glu(1) | 0.99 | Gly(2) | 2.05 |
| Ala(3) | 2.96 | Val(2) | 1.96 |
| Leu(2) | 1.93 | Tyr(1) | 1.01 |
| His(2) | 1.95 | Arg(1) | 1.07 |

Optical rotation: $[\alpha]_D^{27}$= −47° (c=0.1, 1M acetic acid)

Preparation Example 13

Preparation of c-fos (133–150)

The starting resin used was Boc-Ala-OCH$_2$-Pam resin (1% divinylbenzene-crosslinked polystyrene, 0.5 mmol-Boc-Ala, 0.76 mmol/g). Following the general procedure of Preparation Example 1, the amino acid derivatives listed below were successively introduced into the starting material first at the C-terminal. Generally, the coupling reaction was conducted by the symmetric acid anhydride process except for the introduction of Boc-Arg(Tos) and Boc-Asn each of which was used in the form of an acitve ester of 1-hydroxybenzotriazole.

| | Position |
| --- | --- |
| Boc-Arg(Tos)-OH | 8,9,11,12,14 |
| Boc-Asn-OH | 15 |
| Boc-Glu(OBzl)-OH | 3,4,5,6,13 |
| Boc-Ile-OH | 10 |
| Boc-Lys(ε-Cl-Z)-OH | 7,16 |
| Boc-Met-OH | 17 |
| Boc-Pro-OH | 2 |
| Boc-Ser(Bzl)-OH | 1 |

The protected peptide resin resulting from the final coupling reaction was treated with HF in the presence of anisole and methylethylsulfide at 0° C. for 1 hour to remove the protective group and the resin. The peptide was washed with ethyl acetate, dried and extracted with 1M acetic acid containing 0.002% ethanethiol, and the extract was lyophilized to obtain the desired peptide.

Yield :
  Proteded peptide resin: 1.70 g
  Crude peptide: 718.4 mg

The crude peptide (360 mg) was purified by reverse-phase HPLC under the following conditions.
Column: TSK-Gel ODS-120T (21.5×300 mm)
Eluent: 0.01N HCl/CH$_3$CN=95/5→70/30 (30 min)
Detection : 210 nm
Flow rate : 10 ml/min Consequently, 112.5 mg of a purified peptide was obtained. Yield 31.3% based on the crude peptide, or 19.5% based on the starting resin.

The peptide had the following properties.
Rf values:
  Rf$^1$=0.00
  Rf$^2$=0.05

Figure 13:
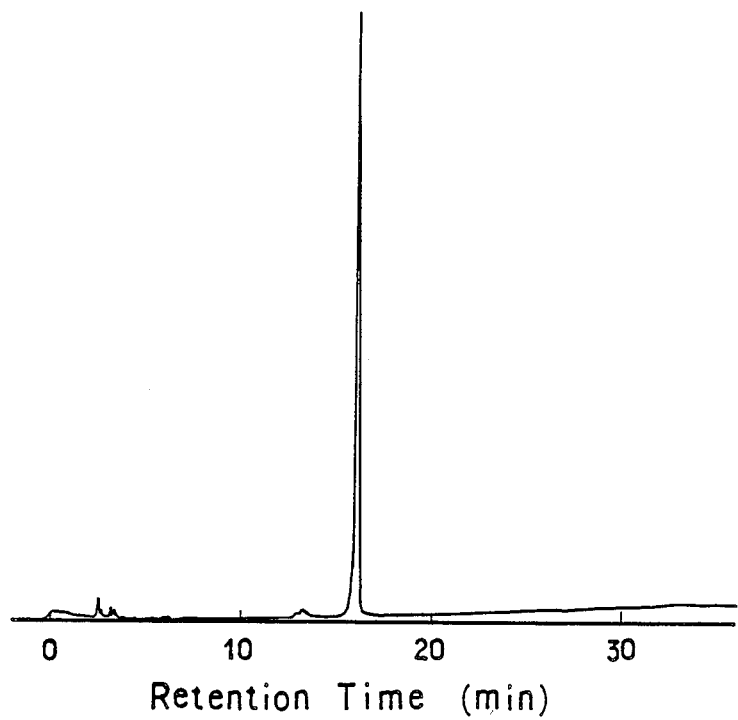

Analysis by HPLC:
FIG. 13 shows the result of HPLC (eluent 0.01N HCl/CH$_3$CN=95/5→75/25, 30 min, detection 210 nm, flow rate 1.0 ml/min) using YMC Pack R-ODS-5 (4.6×25 cm).

Amino acid analysis values:

| Amino acid | Value | Amino acid | Value |
| --- | --- | --- | --- |
| Asp(1) | 1.09 | Ser(1) | 0.88 |
| Glu(5) | 5.01 | Ala(1) | 1.03 |
| Met(1) | 0.97 | Ile(1) | 1.03 |
| Lys(2) | 1.98 | Arg(5) | 5.01 |

Optical rotation: $[\alpha]_D^{24}$= −63° (c=0.1, 1M acetic acid)

Preparation Example 14

Preparation of c-fos (151–163)

The starting resin used was Boc-Asp(OBzl)-OCH$_2$Pam resin (1% divinylbenzene-crosslinked polystyrene, 0.5 mmol-Boc-Asp(OBzl), 0.77 mmol/g). Following the general procedure of Preparation Example 1, the amino acid derivatives listed below were successively introduced into the starting material first at the C-terminal. Generally, the coupling reaction was conducted by the symmetric acid anhydride process except for the introduction of Boc-Arg(Tos) and Boc-Asn each of which was used in the form of an acitve ester of 1-hydroxybenzotriazole.

| | Position |
| --- | --- |
| Boc-Ala-OH | 1,2 |
| Boc-Arg(Tos)-OH | 5,7,8,9 |
| Boc-Asn-OH | 6 |
| Boc-Cys(4-MeBzl)-OH | 4 |
| Boc-Glu(OBzl)-OH | 10 |
| Boc-Leu-OH | 11 |
| Boc-Lys(ε-Cl-Z)-OH | 3 |

| | Position |
|---|---|
| Boc-Thr(Bzl)-OH | 12 |

The protected peptide resin resulting from the final coupling reaction was treated with HF in the presence of anisole at 0° C. for 1 hour to remove the protective group and the resin. The peptide was further treated with a 1:1 mixture of HF and anisole at 0° C. for 1 hour to remove the 4-MeBzl group for the Cys residue, washed with ethyl acetate, dried and extracted with 1M acetic acid, and the extract was lyophilized to obtain the desired peptide.

Yield :
Proteded peptide resin: 1.40 g
Crude peptide: 600.0 mg

The crude peptide (150 mg) was purified by reverse-phase HPLC under the following conditions.
Column : TSK-Gel ODS-120T (2.1×30 cm)
Eluent : 0.01N HCl/CH$_3$CN=95/5→80/20 (30 min)
Detection : 210 nm
Flow rate : 10 ml/min Consequently, 32.4 mg of a purified peptide was obtained Yield 21.6% based on the crude peptide, or 16.3% based on the starting resin.

Figure 14:
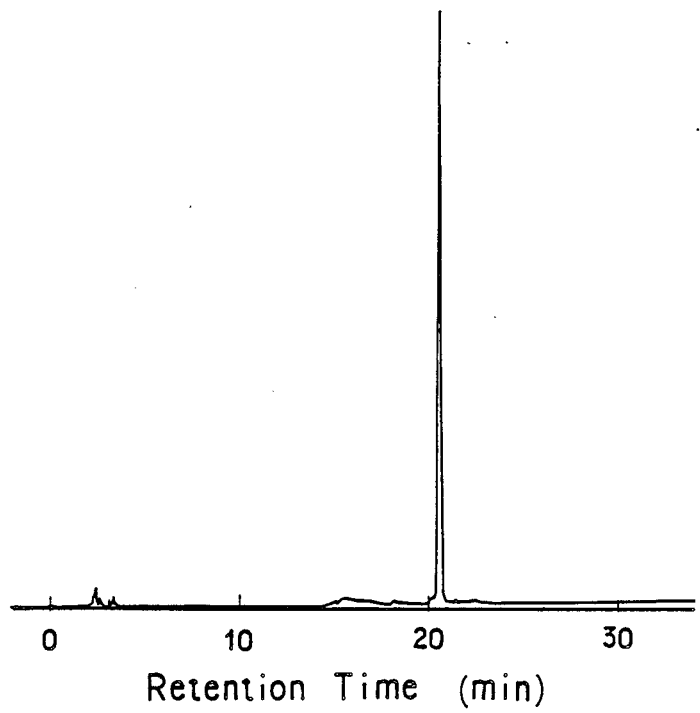

The peptide had the following properties.
Rf values:
Rf$^1$=0.00
Rf$^2$=0.04
Analysis by HPLC:
FIG. 14 shows the result of HPLC (eluent 0.01N HCl/CH$_3$CN=100/0→85/15, 30 min, detection 210 nm, flow rate 1.0 ml/min) using YMC Pack R-ODS-5 (4.6×25 cm).
Amino acid analysis values:

| Amino acid | Value | Amino acid | Value |
|---|---|---|---|
| Asp(2) | 1.99 | Thr(1) | 0.97 |
| Glu(1) | 1.04 | Gly(2) | 2.01 |
| Leu(1) | 1.06 | Lys(1) | 0.92 |
| Arg(4) | 4.00 | | |

Optical rotation: $[\alpha]_D^{24} = -69°$ (c=0.1, 1M acetic acid)

Preparation Example 15

Preparation of c-fos (169–180)

The starting resin used was Boc-Gln-OCH$_2$-Pam resin (1% divinylbenzene-crosslinked polystyrene, 0.5 mmol-Boc-Gln, 0.69 mmol/g). Following the general procedure of Preparation Example 1, the amino acid erivatives listed below were successively introduced into the starting material first at the C-terminal. Generally, the coupling reaction was conducted by the symmetric acid anhydride process except for the introduction of Boc-Gln which was used in the form of an acitve ester of 1-hydroxybenzotriazole.

| | Position |
|---|---|
| Boc-Ala-OH | 10 |
| Boc-Asp(OBzl)-OH | 2,6 |
| Boc-Glu(OBzl)-OH | 5,7 |
| Boc-Gln-OH | 3 |
| Boc-Leu-OH | 4,11 |
| Boc-Lys(ε-Cl—Z)-OH | 8 |
| Boc-Ser(Bzl)-OH | 9 |

| | Position |
|---|---|
| Boc-Thr(Bzl)-OH | 1 |

The protected peptide resin resulting from the final coupling reaction was treated with HF in the presence of anisole at −20° C. for 30 minutes and then at 0° C. for 30 minutes to remove the protective group and the resin. The peptide was washed with ethyl acetate, dried and extracted with dimethylformamide containing 5% of water. The extract was concentrated under reduced pressure and the concentrate was solidified with ethyl acetate to obtain the desired peptide.

Yield:
Proteded peptide resin: 1.21 g
Crude peptide: 480.0 mg

The crude peptide (200 mg) was purified by reverse-phase HPLC under the following conditions.
Column: TSK-Gel ODS-120T (21.5×300 mm)
Eluent: 0.01N HCl/CH$_3$CN=90/10→70/30 (30 min)
Detection: 214 nm
Flow rate: 10 ml/min Consequently, 45.5 mg of a purified peptide was obtained. Yield 22.8% based on the crude peptide, or 15.9% based on the starting resin.

Figure 15:
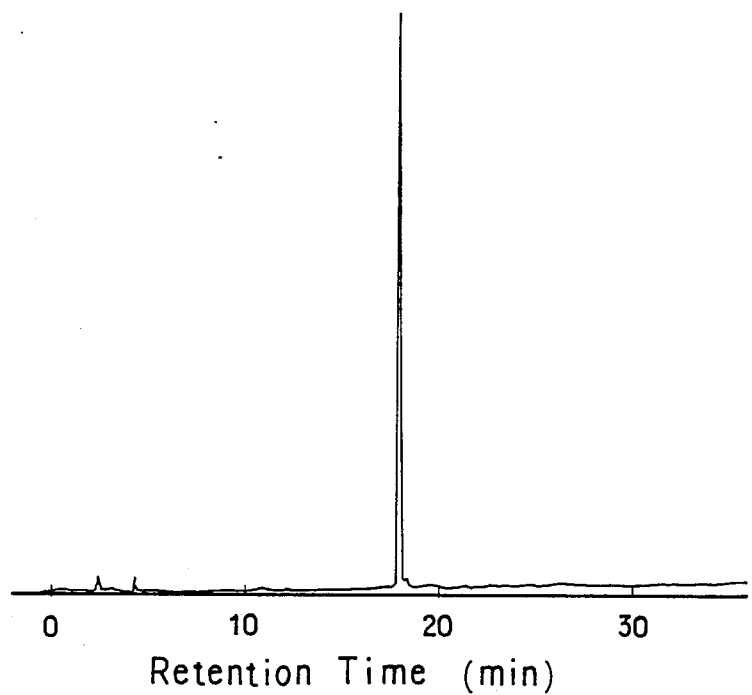

The peptide had the following properties.
Rf values:
Rf$^1$=0.05
Rf$^2$=0.00
Analysis by HPLC:
FIG. 15 shows the result of HPLC (eluent 0.01N HCl/CH$_3$CN=90/10→75/25, 30 min, detection 210 nm, flow rate 1.0 ml/min) using YMC Pack R-ODS-5 (4.6 ×25 cm).
Amino acid analysis values:

| Amino acid | Value | Amino acid | Value |
|---|---|---|---|
| Asp(2) | 1.97 | Thr(1) | 0.89 |
| Ser(1) | 0.94 | Glu(4) | 4.01 |
| Ala(1) | 1.03 | Leu(2) | 2.11 |
| Lys(1) | 1.05 | | |

Optical rotation: $[\alpha]_D^{27} = -55°$ (c=0.1, 50% acetic acid)

Preparation Example 16

Preparation of HPV 18 (E6) (41–57)

The starting resin used was Boc-Leu-OCH$_2$-Pam resin (1% divinylbenzene-crosslinked polystyrene, 0.5 mmol-Boc-Leu, 0.77 mmol/g). Following the general procedure of Preparation Example 1, the amino acid derivatives listed below were successively introduced into the starting material first at the C-terminal. Generally, the coupling reaction was conducted by the symmetric acid anhydride process except for the introduction of Boc-Arg(Tos) and Boc-Asn each of which was used in the form of an acitve ester of 1-hydroxybenzotriazole.

| | Position |
|---|---|
| Boc-Ala-OH | 13 |
| Boc-Arg(Tos)-OH | 6,7,15 |
| Boc-Asp(OcHex)-OH | 11,16 |
| Boc-Glu(OBzl)-OH | 8 |
| Boc-Gln-OH | 2,3 |

| | Position |
|---|---|
| Boc-Leu-OH | 4,5 |
| Boc-Lys(ε-Cl—Z)-OH | 1 |
| Boc-Phe-OH | 12,14 |
| Boc-Tyr(2-Br—Z)-OH | 10 |
| Boc-Val-OH | 9 |

The protected peptide resin resulting from the final coupling reaction was treated with HF in the presence of anisole at −20° C. for 30 minutes and then at 0° C. for 30 minutes to remove the protective group and the resin. The peptide was washed with ethyl acetate, dried and extracted with 1M acetic acid, and the extract was lyophilized to obtain the desired peptide.

Yield:
  Proteded peptide resin: 1.73 g
  Crude peptide: 430.0 mg (from 850 mg of the protected peptide resin)

The crude peptide (190 mg) was purified by reverse-phase HPLC under the following conditions.
Column: TSK-Gel ODS-120T (21.5×300 mm)
Eluent: 0.01N HCl/CH$_3$CN=75/25→50/50 (30 min)
Detection: 210 nm
Flow rate: 10 ml/min The peptide thus partially purified was further purified by reverse-phase HPLC under the following condition.
Column: YMC Pack D-ODS-5 (20.0×250 mm)
Eluent: 0.01N HCl/CH$_3$CN=80/20→60/40 (30 min)
Detection: 210 nm
Flow rate: 10 ml/min Consequently, 48.4 mg of a purified peptide was obtained. Yield 25.5% based on the crude peptide, or 20.3% based on the starting resin.

Figure 16:
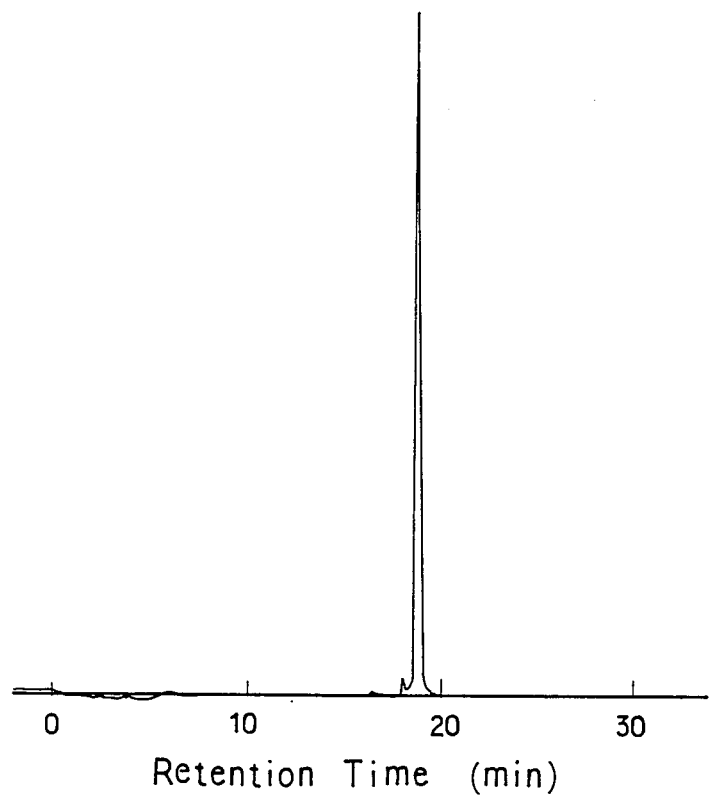

The peptide had the following properties.
Rf values:
  Rf$^1$=0.00
  Rf$^2$=0.00
Analysis by HPLC:
FIG. 16 shows the result of HPLC (eluent 0.01N HCl/CH$_3$CN=85/15→65/35, 30 min, detection 210 nm, flow rate 1.0 ml/min) using TSK Gel ODS-120T (4.6×25 cm).
Amino acid analysis values:

| Amino acid | Value | Amino acid | Value |
|---|---|---|---|
| Asp(2) | 1.98 | Glu(3) | 2.94 |
| Ala(1) | 1.02 | Val(1) | 1.04 |
| Leu(3) | 3.09 | Tyr(1) | 1.04 |
| Phe(2) | 2.04 | Lys(1) | 0.93 |
| Arg(3) | 2.91 | | |

Optical rotation: $[\alpha]_D^{25}$ = −45° (c=0.1, 1M acetic acid)

Preparation Example 17

Preparation of c-raf-1 (398–421)

The starting resin used was Boc-Phe-OCH$_2$-Pam resin (1% divinylbenzene-crosslinked polystyrene, 0.5 mmol-Boc-Phe, 0.80 mmol/g). Following the general procedure of Preparation Example 1, the amino acid derivatives listed below were successively introduced into the starting material first at the C-terminal. Generally, the coupling reaction was conducted by the symmetric acid anhydride process except for the introduction of Boc-Arg(Tos) and Boc-Asn each of which was used in the form of an active ester of 1-hydroxybenzotriazole.

| | Position |
|---|---|
| Boc-Ala-OH | 4,5,12 |
| Boc-Arg(Tos)-OH | 3,20 |
| Boc-Asp(OBzl)-OH | 9 |
| Boc-Asn-OH | 11 |
| Boc-Cys(4-MeBzl)-OH | 13 |
| Boc-Glu(OBzl)-OH | 8 |
| Boc-His(Tos)-OH | 2,6 |
| Boc-Ile-OH | 10 |
| Boc-Leu-OH | 1,15,21 |
| Boc-Pro-OH | 19,22 |
| Boc-Ser(Bzl)-OH | 18 |
| Boc-Thr(Bzl)-OH | 7,14,16,17 |
| Boc-Val-OH | 23 |

The protected peptide resin resulting from the final coupling reaction was treated with HP in the presence of anisole at −20° C. for 30 minutes and then at 0° C. for 30 minutes to remove the protective group and the resin. The peptide was further treated with a 1:1 mixture of HF and anisole at 0° C. for 1 hour to remove the 4-MeBzl group from the Cys residue, washed with ethyl acetate, dried and extracted with 3M acetic acid, and the extract was lyophilized to obtain the desired peptide.

Yield:
  Protected peptide resin: 1.40 g
  Crude peptide: 600.0 mg

The crude peptide (150 mg) was purified by reverse-phase HPLC under the following conditions.
Column: TSK-Gel ODS-120T (21.5×300 mm)
Eluent: 0.01N HCl/CH$_3$CN=95/5→80/20 (30 min)
Detection: 210 nm
Flow rate: 10 ml/min Consequently, 21.0 mg of a purified peptide was obtained. Yield 5.4% based on the crude peptide, or 1.6% based on the starting resin.

Figure 17:
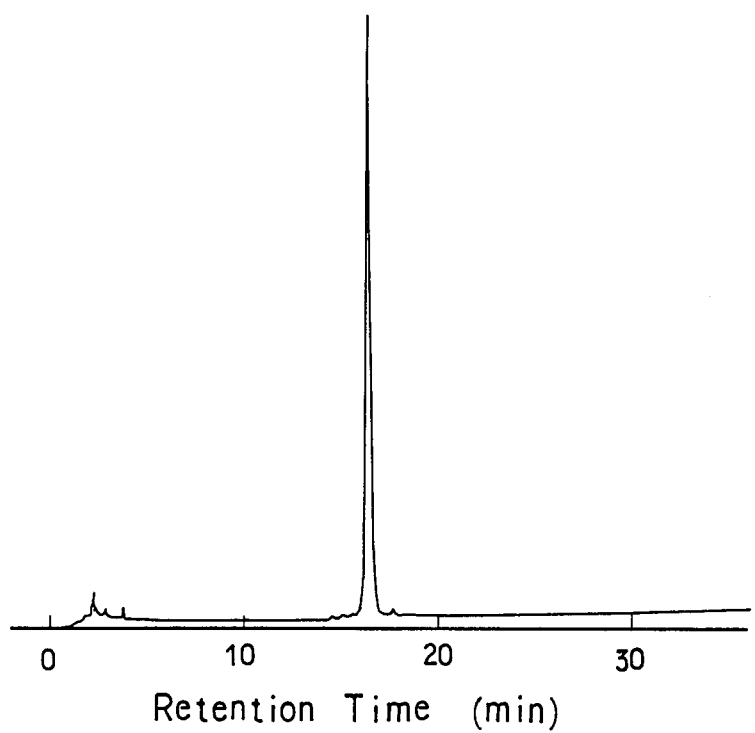

The peptide had the following properties.
Rf values:
  Rf$^1$=0.00
  Rf$^2$=0.00
Analysis by HPLC:
FIG. 17 shows the result of HPLC (eluent 0.01N HCl/CH$_3$CN=80/20→60/40, 30 min, detection 210 nm, flow rate 1.0 ml/min) using YMC Pack R-ODS-5 (4.6×25 cm).
Amino acid analysis values:

| Amino acid | Value | Amino acid | Value |
|---|---|---|---|
| Asp(2) | 1.93 | Thr(4) | 3.40 |
| Ser(1) | 0.68 | Glu(1) | 0.94 |
| Ala(3) | 2.85 | Val(1) | 1.17 |
| Ile(1) | 1.09 | Leu(3) | 2.78 |
| Phe(1) | 1.00 | His(2) | 2.27 |
| Arg(2) | 1.90 | | |

Optical rotation: $[\alpha]_D^{27}$ = −34° (c=0.1, 1M acetic acid)

Preparation Example 18

Following the general procedure of Preparation Example 12 and using appropriate starting materials, the peptides listed below were prepared.

h-TGF-α (1–7)

This peptide had the following properties.

Optical rotation: $[\alpha]_D^{26.5} = -29°$ (c=0.1, 50% acetic acid)
Rf values:
Rf$^1$=0.02
Rf$^2$=0.29
Amino acid analysis values:

| Amino acid | Value | Amino acid | Value |
|---|---|---|---|
| Asp(2) | 2.07 | Ser(1) | 0.96 |
| Val(2) | 1.63 | Phe(1) | 1.12 |
| His(1) | 1.02 | | | c-raf-1 (1–22)

This peptide had the following properties.
Optical rotation: $[\alpha]_D^{26} = -69.7°$ (c=0.1, 3M acetic acid)
Rf values:
Rf$^1$=0.00
Rf$^2$=0.18
Amino acid analysis values:

| Amino acid | Value | Amino acid | Value |
|---|---|---|---|
| Asp(1) | 1.11 | Pro(2) | 1.96 |
| Phe(2) | 2.06 | Thr(3) | 2.81 |
| Gly(1) | 1.05 | His(2) | 2.00 |
| Ser(6) | 5.70 | Ala(1) | 1.00 |
| Arg(1) | 0.98 | Glu(2) | 2.03 |
| Tyr(1) | 1.00 | | | c-raf-1 (142–170)

This peptide had the following properties.
Optical rotation: $[\alpha]_D^{\approx} = -92.3°$ (c=0.1, 3M acetic acid)
Rf values:
Rf$^1$=0.00
Rf$^2$=0.37
Amino acid analysis values:

| Amino acid | Value | Amino acid | Value |
|---|---|---|---|
| Asp(3) | 3.01 | Gly(1) | 0.75 |
| Leu(2) | 2.25 | Arg(1) | 1.21 |
| Thr(1) | 0.92 | Ala(3) | 3.21 |
| Phe(2) | 2.01 | Glu(4) | 4.20 |
| Val(6) | 5.98 | His(1) | 0.94 |
| Pro(2) | 1.62 | Ile(1) | 1.10 |
| Lys(2) | 1.80 | | |

N-myc (48–69)

This peptide had the following properties.
Optical rotation: $[\alpha]_D^{26.5} = -56°$ (c=0.1, 50% acetic acid)
Rf values:
Rf$^1$=0.04
Rf$^2$=0.37
Amino acid analysis values:

| Amino acid | Value | Amino acid | Value |
|---|---|---|---|
| Asp(1) | 1.10 | Pro(2) | 1.63 |
| Met(1) | 0.99 | Thr(1) | 1.09 |
| Gly(1) | 1.06 | Leu(3) | 3.09 |
| Ser(3) | 2.64 | Ala(1) | 1.09 |
| Phe(1) | 1.02 | Glu(5) | 4.97 |
| Val(1) | 1.16 | His(1) | 1.16 |

HTLV-PX-I

This peptide had the following properties.
Optical rotation: $[\alpha]_D^{25} = -70.7°$ (c=0.1, 3M acetic acid)
Rf values:
Rf$^1$=0.07
Rf$^2$=0.28
Amino acid analysis values:

| Amino acid | Value | Amino acid | Value |
|---|---|---|---|
| Asp(2) | 2.11 | Gly(1) | 1.08 |
| Thr(1) | 1.00 | Ile(2) | 1.92 |
| Glu(2) | 2.01 | His(1) | 0.97 |
| Pro(2) | 1.90 | Arg(1) | 1.00 |

HTLV-PX-II

This peptide had the following properties.
Optical rotation: $[\alpha]_D^{25} = -83.5°$ (c=0.1, 1M acetic acid)
Rf values:
Rf$^1$=0.00
Rf$^2$=0.36
Amino acid analysis values:

| Amino acid | Value | Amino acid | Value |
|---|---|---|---|
| Thr(3) | 2.70 | Ile(1) | 0.92 |
| Arg(2) | 1.96 | Ser(2) | 1.86 |
| Leu(2) | 2.04 | Glu(1) | 1.14 |
| Phe(1) | 0.99 | Pro(3) | 2.91 |
| Lys(2) | 2.03 | | |

<PREPARATION OF IMMUNOGENS>

Preparation Example A

The peptide c-myc (11-24) of the present invention (obtained in Preparation Example 11) was bound to porcine thyroglobulin by the carbodiimide process (Science, 144, 1344–1346 (1964)) to obtain an immunogen (hereinafter referred to as "Antigen A").

Preparation Example B

The peptide c-myc (423–437) obtained in Preparation Example 6 according to the present invention was bound to ascaris protein in the same manner as in Preparation Example A above to obtain an immunogen (hereinafter referred to as "Antigen B").

<PREPARATION OF ANTIBODIES>

Preparation Example (a)

For immunization, six guinea pigs were subcutaneously injected with 45 μg of Antigen (calculated as c-myc (11-24)) and the same amount of complete Freund's adjuvant. Three additional injections of Antigen A were thereafter similarly given at the same dose at 4-week intervals. Consequently, four of the six test animals produced the desired antibody. The total blood was collected from these four animals and centrifuged to obtain the desired antiserum (antibody), which will be hereinafter referred to as "Antibody A".

Preparation Example (b)

Rabbits were immunized with Antibody B in the same manner as in Preparation Example (a) to obtain the desired antiserum (antibody), which will be hereinafter referred to as "Antibody B".

<PREPARATION OF LABELED PEPTIDE>

The peptide c-myc (11-24) obtained Preparation Example 11 according to the invention was labeled with Na($^{125}$I) by the chloramin-T method (Nature, 194, 495-496 (1962)) and then purified by gel filtration (Sephadex G-10 (product of Pharmacia) column, 0.9×15 cm, 1N acetic acid) to prepare $^{125}$I-labeled peptide (tracer).

The labeled peptide was 15 to 20 μCi/μg in specific activity.

<PREPARATION OF CALIBRATION CURVE>

The peptide c-myc (11-24) was used as the standard. The standard diluent used was 0.1M sodium phosphate buffer (pH 7.4) containing 0.02M EDTA-4Na, 0.027M EDTA-2Na, 0.0 , 0.1% BSA (bovine serum albumin) and 250KIU (kallikrein inactivator units)/ml Trasylol (Bayer). A standard curve (calibration curve) was prepared using Antibody A obtained in Preparation Example (a) and the $^{125}$I-labeled peptide (tracer).

Figure 18:
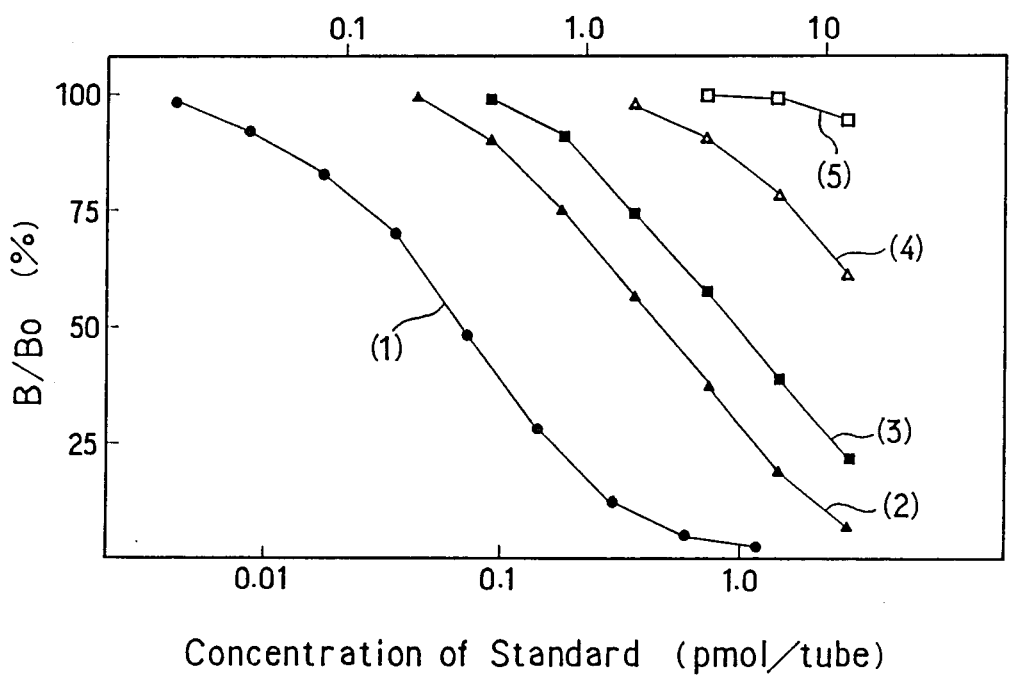
FIG. 18 shows the standard curve (calibration curve) of an antibody obtained using the peptide of the invention and dose-dependent curves of various human cancer-related protein samples.

The curve is indicated at (1) in FIG. 18, in which the concentration (pmol/tube) of c-myc (11-24) is plotted as abscissa vs. B/Bo (%) as ordinate.

<TEST FOR DETERMINATION OF HUMAN CANCER-RELATED PROTEINS USING ANTIBODY A>

The samples used were extracts of the following four human cancer tissues and a human heart tissue (right auricle tissue removed by cardiac operation).
HL-60 (Nature, 299, 61-63 (1982))
N231 (Nature, 306, 194-196 (1983))
H69 (same as above)
Lu-65 (EMBO J., 3, 2943-2946 (1984))

The cancer tissues were prepared by transplanting the tumors into nude mice and removing the grown tumors. Each of the sample tissues was cut into small pieces, suspended in RIPA buffer (0.05M Tris-HCl buffer, pH 7.5, containing 0.15M NaCl, 0.1% SDS, 1% Triton X-100, 0.5% sodium deoxycholate and 1 mM phenylmethylsulfonylfluoride) to a concentration of 0.25 g/ml and then sonicated for 20 to 30 seconds (Branson Sonifier Cell Disruptor 185, product of Branson Sonic Power Company, U.S.A.). The resulting extract was centrifuged at 1000×g for 20 minutes, and the supernatant was preserved at −80° C. for use as a sample.

Each sample thus prepared was serially diluted twofold or more with the standard diluent, and 0.1 ml of each dilution was used for RIA. Curves (2) to (5) in FIG. 18 show the results (dose response curves). The results achieved by the samples are represented by curve (2) for HL-60 sample, curve (3) for N231 sample, curve (4) for Lu-65 sample, and curve (5) for H69 sample and heart tissue sample.

FIG. 18 reveals that the dose response curves (curves (2) to (4)) of the HL-60, N231 and Lu-65 extract samples are in parallel with the curve of c-myc (11-24), indicating that the immunoreactive substance present in each of these samples can be determined by RIA. No c-myc gene product was detected from the H69 sample or heart tissue sample.

The extract samples of the HL-60, N231 and Lu-65 tissues which are known to have c-myc gene amplification were found to contain the immunoreactive substance in an amount of 33 pmols, 18 pmols and 3.7 pmols, respectively, calculated as c-myc (11-24), per gram of the tissue, whereas the corresponding values for the H69 and heart tissue samples having no such amplification were less than 1.6 pmols (detection limit).

<TEST BY PEROXIDASE-ANTIPEROXIDASE (PAP) METHOD USING ANTIBODY>

The liver, kidney, stomach and small intestine were collected from five human fetuses (at intermediate stages of gestation, weighing 400 to 810 g) 1 to 6 hours after death following therapeutic or spontaneous abortion. Normal tissues of the liver and kidney were taken from five human adults at autopsy. In addition, a tumor tissue (obtained from a transplant in a nude mouse) of Lu-65, which has been proved to have c-myc gene amplification, was used as a positive control.

These tissues were fixed in Bouin's fluid for about 4 hours, dehydrated through an ethanol-xylene series and embedded in paraffin. Dewaxed paraffin sections were submitted to the peroxidase-antiperoxidase (PAP) method for staining test using Antibody B (at a dilution of 1:3000) prepared in Preparation Example (b).

The antibody was found to stain the cellular elements of Lu-65. The staining was perfectly blocked by preincubation of the antibody with 5 μg of c-myc (423-437), while the staining was unaffected by the pretreatment of the antibody with 10 μg of ascaris protein.

The immunoreaction product was present both granularly and diffusely in the cytoplasm, whereas the nuclei were free from any detectable immunoreactivity.

In the human fetuses examined, a positive immunoreaction was found in the cellular elements in the liver and kidney. No immunoreaction was found within sinusoids or in the interlobular connective tissues.

In the kidney, the immunoreactivity was localized in the epithelium of the proximal convolution. In the liver and kidney, immunoreactivity was found in the cytoplasm, whereas the nuclei showed no detectable immunoreactivity.

No immunopositive cells were found in the stomach or small intestine of the fetuses.

In the adult human liver, only a very few of the hepatocytes were immunoreactive, with the immunoreactivity restricted only to the cytoplasm. The urinary tubules in the adult kidney were immunoreactive as observed in the fetal tissues.

<IMMUNOCHEMICAL STUDY OF c-myc PROTEIN IN THE CHEMICALLY INDUCED LIVER CANCER TISSUE OF RATS>

(1) Male Wister rats (weighing 150 g) were fed with feedstuff containing 0.06% 3'-methyl-4-dimethylaminoazobenzene (3'-Me-DAB), and decapitated daily after 18 hours of fasting and the liver tissue was removed. Each of the liver tissues was cut into small pieces, uniformly suspended in an aqueous solution containing 50 mM Tris buffered-saline, 5% glycerol, 250 KIU/ml aprotinin and 0.1 mM phenyl-methyl-sulfonyl-fluoride (PMSF), to a concentration of 0.1 g/ml, and then sonicated for 20 to 30 seconds (Branson Sonifier Cell Disruptor 185). The resulting extract was centrifuged at 140,000 g for 1 hour to obtain a supernatant which was used as a sample.

Figure 19:
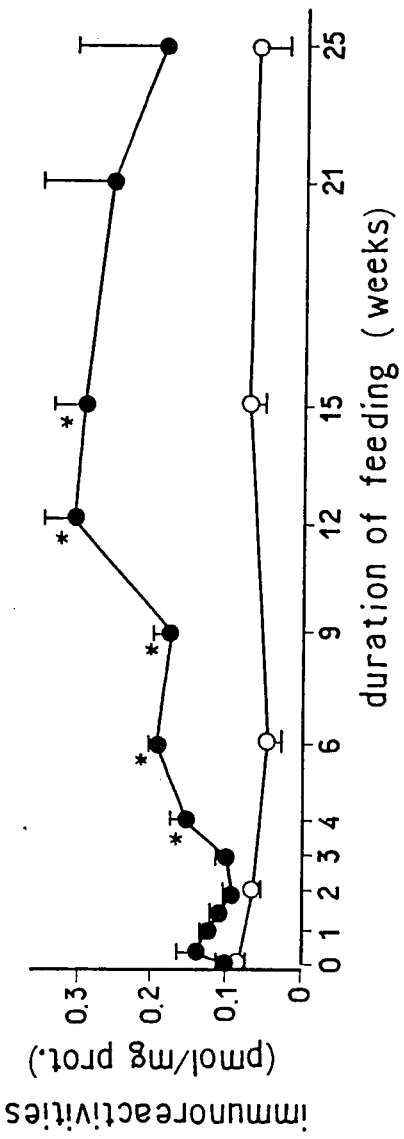
FIG. 19 shows the results of RIA using an antibody of the invention with respect to the c-myc protein in a chemically induced liver cancer tissue of rats.

The c-myc protein in the sample was immunochemically monitored by the C-terminal-specific RIA with use of the anti-c-myc (423-437) serum (i.e., Antibody B) prepared in Preparation Example (b). The results are shown in FIG. 19 in which the line (●—) shows the results obtained using the liver tissues of 3-Me-DAB feed rats; the asterisk (*) indicates significant increase of the amount of the c-myc immunoreactivities; and the line (○—○) shows the results obtained using the liver tissues of control rats which did not receive 3'-Me-DAB. As seen from FIG. 19, the c-myc protein-related immunoreactivity tended to slightly increase at foremost initial stage and then significantly increased after 4 weeks when there occurred marked degrees of nodal growth and regeneration of liver tissues. The immunoreactivity further increased in 12 weeks in parallel with the development of the nodal grown portion and regenerated nodal portion, but rather tended to decrease after 20 weeks when the canceration of tissues progressed.

These results show that the use of Antibody B of the present invention enables detection of liver oncogene product.

(2) Liver tissues of rats were obtained in the same manner as in (1) above and immunohistochemically observed using Antibody B of the invention by the peroxidase-antiperoxidase (PAP) method following the general procedure described in <TEST BY PEROXIDASEANTIPEROXIDASE (PAP) METHOD USING ANTIBODY> above.

Consequently a noticeably large quantity of modified liver cells was found 3 weeks after administration of 3'-Me-DAB, while the c-myc protein-positive reaction was detected only in the medium-to-large size remaining cells. After six weeks when nodal growth was observed, many c-myc protein-positive tissues were detected in the grown portion of tissues, and the remaining cells were also positive. In 21 weeks, liver cancer apparently developed. Even at this stage, c-myc protein-positive reaction was seen in the nodal grown portion and regenerated liver tissue portion while only a very few positive cells were detected in cancer tissues.

From these results, the detection of c-myc-related protein by the specific RIA or immunohistochemistry using Antibody B of the invention is useful for demonstrating the increasing c-myc protein in the liver.

We claim:

1. An oncogene-related peptide characterized in that the peptide comprises a portion of the amino acid sequence of a gene product coded for by an oncogene wherein the peptide is selected from the group consisting of:

H-Arg-Ser-Ser-Arg-Thr-Arg-Arg-Glu-Thr-Gln-Leu-OH,

H-Tyr,Glu-Ser-Tyr-Lys-Try-Pro-Met-Phe-Ile-Ala-Leu-Ser-Lys-Asn-Gly-Lys-Thr-OH,

H-His-Ala-Asp-Thr-Arg-Asp-Ser-Leu-Leu-Glu-Leu-Ser-Pro-Val-Glu-Arg-Gly-Val-Val-Ser-Ile-Phe-Gly-Val-Ala-Ser-OH,

H-Lys-Gln-Gln-Leu-Leu-Arg-Arg- Glu-Val-Tyr-Asp-Phe-Ala-Phe-Arg-Asp-Leu-OH,

H—Val—Cys—His—Ser—Gly—Tyr—Val—Gly—Ala—
　　　　　　|
Arg—Cys—Glu—His—Ala—Asp—Leu—Leu—Ala—OH,

H-Ser-Pro-Glu-Glu-Glu-Glu-Lys-Arg-Arg-Ile-Arg-Arg-Glu-Arg-Asn-Lys-Met-Ala-OH,

H-Ala-Ala-Lys-Cys-Arg-Asn-Arg-Arg-Arg-Glu-Leu-Thr-Asp-OH,

H-Thr-Asp-Gln-Leu-Glu-Asp-Glu-Lys-Ser-Ala-Leu-Gln-OH,

H-Leu-His-Arg-Ala-Ala-His-Thr-Glu-Asp-Ile-Asn-Ala-Cys-Thr-Leu-Thr-Thr-Ser-Pro-Arg-Leu-Pro-Val-Phe-OH,

H-Val-Val-Ser-His-Phe-Asn-Asp-OH,

H-Ser-Gln-His-Arg-Tyr-Ser-Thr-pro-His-Ala-Phe-Thr-Phe-Asn-Thr-Ser-Ser-Pro-Ser-Glu-Gly-OH, H-His-Gly-Asp-Val-Ala-Val-Lys-Ile-Leu-Lys-Val-Val-Asp-Pro-Thr-Pro-Thr-Pro-Glu-Gln-Phe-Gln-Ala-Phe-Arg-Asn-Glu-Val-Ala-Val-Leu-OH, H-Gly-Phe-Ala-Glu-His-Ser-Ser-Glu-Pro-Pro-Ser-Trp-–Glu-Met-Leu-Leu-Glu-Asn-Glu-Leu-OH, and H-Ile-Pro-Arg-Leu-Pro-Ser-Phe-Pro-Thr-Gln-Arg-Thr-Ser-Lys-Thr-Leu-Lys-OH.

2. A peptide as defined in claim 1 which is H-Arg-Ser-Ser-Arg-Thr-Arg-Arg-Glu-Thr-Gln-Leu-OH.

3. A peptide as defined in claim 1 which is H-Tyr-Glu-Ser-Tyr-Lys-Tyr-Pro-Gly-Met-Phe-Ile-Ala-Leu-Ser-Lys-Asn-Gly-Lys-Thr-OH.

4. A peptide as defined in claim 1 which is H-Ala-Asp-Thr-Arg-Asp-Ser-Leu-Leu-Glu-Leu-Ser Pro Val Glu Arg-Gly-Val-Val-Ser-OH.

5. A peptide as defined in claim 1 which is H-Lys-Gln-Gln-Leu-Leu-Arg-Arg-Glu-Val-Tyr-Asp-Phe-Ala-Phe-Arg-Asp-Leu-OH.

6. A peptide as defined in claim 1 which is

H—Val—Cys—His—Ser—Gly—Tyr—Val—Gly—Ala—
　　　　　　|
Arg—Cys—Glu—His—Ala—Asp—Leu—Leu—Ala—OH.

7. A peptide as defined in claim 1 which is H-Ser-Fro-Glu-Glu-Glu-Glu-Lys-Arg-Arg-Ile-Arg-Arg-Glu-Arg-Asn-Lys-Met-Ala-OH.

8. A peptide as defined in claim 1 which is H-Ala-Ala-Lys-Cys-Arg-Asn-Arg-Arg-Arg-Glu-Leu-Thr-Asp-OH.

9. A peptide as defined in claim 1 which is H-Thr-Asp-Gln-Leu-Glu-Asp-Glu-Lys-Ser-Ala-Leu-Gln-OH.

10. A peptide as defined in claim 1 which is H-Leu-His-Arg-Ala-Ala-His-Thr-Glu-Asp-Ile-Asn-Ala-Cys-Thr-Leu-Thr-Thr-Ser-Pro-Arg-Leu-Pro-Val-Phe-OH.

11. A peptide as defined in claim 1 which is H-Val-val-Ser-His-Phe-Asn-Asp-OH.

12. A peptide asdefined in claim 1 which is H-Ser-Gln-His-Arg-Tyr-Ser-Tr-Pro-His-Ala-Phe-Thr-Phe-Asn-Thr-Ser-Ser-Pro-Ser-Ser-Gly-Gly-OH.

13. A peptide as defined in claim 1 which is H-His-Gly-Aspo-Val-Ala-Val-Lys-Ile-Leu-Lys-Val-Val-Asp-Pro-Thr-Pro-Glu-Gln-Phe-Gln-Ala-Phe-Arg-Asn-Glu-Val-Ala-Val-Leu-OH.

14. A peptide as defined in claim 1 which is H-Gly-Phe-Ala-Glu-His-Ser-Ser-Glu-Pro-Pro-Ser-Trp-Val-Thr-Glu-Met-Leu-Leu-Glu-Asn-Glu-Leu-OH.

15. A peptide as defined in claim 1 which is H-Ile-Pro-Arg-Leu-Pro-Ser-Phe-Pro-Thr-Gln-Arg-Thr-Ser-Lys-Thr-Leu-Lys-OH.

* * * * *